(12) United States Patent
Sargent et al.

(10) Patent No.: US 10,898,137 B2
(45) Date of Patent: Jan. 26, 2021

(54) GEL-ASSISTED ELECTROENCEPHALOGRAM SENSOR ELECTRODE

(71) Applicant: X Development LLC, Mountain View, CA (US)

(72) Inventors: Joseph Hollis Sargent, San Francisco, CA (US); Philip Edwin Watson, Santa Cruz, CA (US)

(73) Assignee: X Development LLC, Mountain View, CA (US)

( * ) Notice: Subject to any disclaimer, the term of this patent is extended or adjusted under 35 U.S.C. 154(b) by 156 days.

(21) Appl. No.: 15/855,923

(22) Filed: Dec. 27, 2017

(65) Prior Publication Data

US 2019/0192078 A1    Jun. 27, 2019

(51) Int. Cl.
*A61B 5/0478*    (2006.01)
*A61B 5/00*    (2006.01)
(Continued)

(52) U.S. Cl.
CPC ........ *A61B 5/6832* (2013.01); *A61B 5/04004* (2013.01); *A61B 5/0478* (2013.01); *A61B 5/04842* (2013.01); *A61B 5/6814* (2013.01); *A61M 35/006* (2013.01); *A61B 5/002* (2013.01); *A61B 5/0006* (2013.01); *A61B 5/04012* (2013.01); *A61B 5/486* (2013.01);
(Continued)

(58) Field of Classification Search
CPC . A61B 5/04026; A61B 5/683; A61B 2562/14; A61M 35/10
USPC ........................................................ 600/386
See application file for complete search history.

(56) References Cited

U.S. PATENT DOCUMENTS 1,230,921 A    6/1917    Paul
4,125,110 A    11/1978    Hymes
(Continued)

FOREIGN PATENT DOCUMENTS

WO    WO2018068013    4/2018

OTHER PUBLICATIONS

Berg et al. "The Cyberlink Interface: Development of a Hands-Free Continuous/Discrete Mutli-Channel Computer Input Device," United Stated Air Force Research Laboratory, AFRL-HE-WP-TR-1999-0191, Feb. 1999, 63 pages.
(Continued)

*Primary Examiner* — Etsub D Berhanu
(74) *Attorney, Agent, or Firm* — Fish & Richardson P.C.

(57) ABSTRACT

An electroencephalogram (EEG) sensor is disclosed. The EEG sensor includes a housing defining a chamber capable of storing a gel, the housing includes a first and a second chamber wall, the walls each comprising a corresponding access port located on a common axis extending through the housing; an electrically-conductive probe with a probe tip extending at least partially through the chamber along the axis, at least a portion of the probe tip being exposed to the chamber; an electrical terminal located at an outer surface of the second chamber wall, the electrical terminal being in electrical communication with the probe tip through the access port at the second chamber wall; and a compliant member mechanically coupled to the access port at the first chamber wall capable of compressing, thereby providing a dispense pathway from the chamber through the access port at the first chamber wall.

19 Claims, 18 Drawing Sheets

(51) Int. Cl.
*A61B 5/0484* (2006.01)
*A61F 13/40* (2006.01)
*A61B 5/04* (2006.01)

(52) U.S. Cl.
CPC ............ *A61B 5/6833* (2013.01); *A61B 5/742* (2013.01); *A61B 5/7405* (2013.01); *A61B 2562/08* (2013.01); *A61B 2562/125* (2013.01); *A61B 2562/14* (2013.01); *A61B 2562/168* (2013.01); *A61M 2230/10* (2013.01)

(56) References Cited

U.S. PATENT DOCUMENTS

| | | | | |
|---|---|---|---|---|
| 4,632,122 | A * | 12/1986 | Johansson | A61B 5/04026 600/383 |
| 4,709,702 | A * | 12/1987 | Sherwin | A61B 5/0478 600/383 |
| D327,325 | S | 6/1992 | Strand | |
| 5,273,037 | A * | 12/1993 | Itil | A61B 5/0478 600/383 |
| 5,404,875 | A * | 4/1995 | Gevins | A61B 5/0478 600/372 |
| D369,667 | S | 5/1996 | Vincents et al. | |
| D378,614 | S | 3/1997 | Jensen | |
| D385,037 | S | 10/1997 | Jensen | |
| 5,823,832 | A * | 10/1998 | Das | A61B 5/0416 439/817 |
| D429,337 | S | 8/2000 | Sanfilippo | |
| 6,175,753 | B1 | 1/2001 | Menkes et al. | |
| 6,574,513 | B1 | 6/2003 | Collura et al. | |
| D478,173 | S | 8/2003 | Nielsen | |
| D478,668 | S | 8/2003 | Epstein | |
| 6,640,122 | B2 | 10/2003 | Manoli et al. | |
| 6,998,031 | B1 | 2/2006 | Hill | |
| D536,673 | S | 2/2007 | Silber | |
| D567,374 | S | 4/2008 | Reznik | |
| D625,823 | S | 10/2010 | Schneider et al. | |
| 8,112,141 | B2 | 2/2012 | Wilson et al. | |
| 9,055,927 | B2 | 6/2015 | Nierenberg et al. | |
| 9,186,084 | B2 | 11/2015 | Chai et al. | |
| 9,232,922 | B2 | 1/2016 | Nierenberg et al. | |
| 9,314,184 | B2 | 4/2016 | Chai et al. | |
| 9,314,185 | B2 | 4/2016 | Chai et al. | |
| D758,595 | S | 6/2016 | Zhao | |
| D768,096 | S | 10/2016 | Fleischer | |
| D783,818 | S | 4/2017 | Hermann et al. | |
| D791,956 | S | 7/2017 | Stewart | |
| 10,716,487 | B2 | 7/2020 | Laszlo et al. | |
| 10,722,134 | B2 | 7/2020 | Watson et al. | |
| 2001/0044573 | A1 * | 11/2001 | Manoli | A61B 5/0478 600/383 |
| 2002/0052610 | A1 | 5/2002 | Skakoon et al. | |
| 2005/0192594 | A1 | 9/2005 | Skakoon et al. | |
| 2007/0255127 | A1 * | 11/2007 | Mintz | A61B 5/0476 600/383 |
| 2008/0269842 | A1 | 10/2008 | Giftakis et al. | |
| 2010/0100001 | A1 | 4/2010 | Aguilar et al. | |
| 2011/0046503 | A1 | 2/2011 | Pradeep et al. | |
| 2011/0125046 | A1 | 5/2011 | Burton et al. | |
| 2012/0035441 | A1 | 2/2012 | Shoshihara et al. | |
| 2013/0110212 | A1 | 5/2013 | Feng et al. | |
| 2014/0316230 | A1 | 10/2014 | Denison et al. | |
| 2014/0347265 | A1 | 11/2014 | Aimone et al. | |
| 2015/0065838 | A1 * | 3/2015 | Wingeier | A61B 5/6814 600/383 |
| 2015/0327789 | A1 | 11/2015 | Sjaaheinn | |
| 2015/0374255 | A1 | 12/2015 | Vasapollo | |
| 2016/0228693 | A1 | 8/2016 | Vardiman | |
| 2018/0085573 | A1 | 3/2018 | Alam | |
| 2019/0192030 | A1 | 6/2019 | Watson et al. | |
| 2019/0192031 | A1 | 6/2019 | Laszlo et al. | |
| 2019/0192075 | A1 | 6/2019 | Kranz | |
| 2019/0239763 | A1 | 8/2019 | Block et al. | |
| 2019/0239807 | A1 | 8/2019 | Watson et al. | |

OTHER PUBLICATIONS

Hasan et al. "Prediction of Epileptic Seizure by Analysing Time Series EEG Signal Using k-NN Classifier," Applied Bionics and Biomechanics, Aug. 2017, 12 pages.

Krishnan et al. "ActiveClean: An Interactive Data Clearning Framework for Modern Machine Learning," SIGMOD, Jun. 2016, 4 pages.

Liao et al. "Gaming control using a wearable and wireless EEG-based brain-computer interface device with novel dry foam-based sensors," Journal of NeuroEngineering and Rehabilitation, 9(5), Jan. 28, 2012, 12 pages.

Ries et al. "Response-Locked Brain Dynamics of Word Production," PLoS One, 8(3), Mar. 12, 2013, 14 pages.

Telpaz et al. "Using EEG to predict consumers' future choices," Journal of Marketing Research, 52(4), Aug. 2015, 60 pages.

McNall, "How do you clean a patient's head after removing EEG electrodes?" ASET Department of Education Report, retrieved from URL <https://asetdeptedu.blogspot.com/2014/04/how-do-you-clean-patients-head-after html>, Apr. 17, 2014, retrieved Apr. 17, 2020, 3 pages.

www.frontiernerds.com [online] "How to Hack Toy EEGs," Apr. 7, 2010, [retrieved on Apr. 16, 2020] Retrieved from Internet: URL<http://www.frontiernerds.com/brain-hack> 92 pages.

* cited by examiner

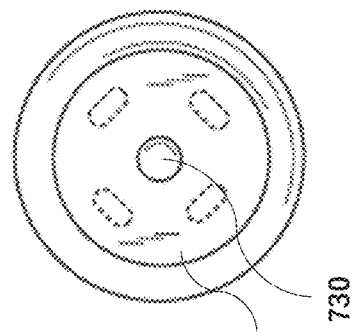
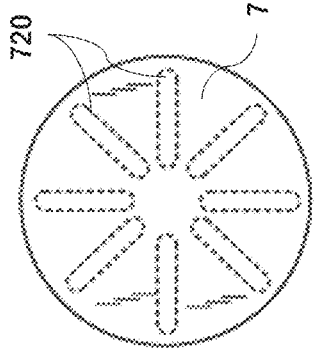
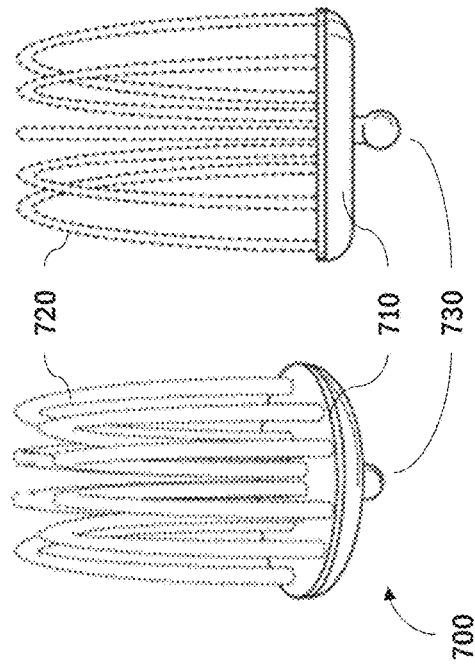
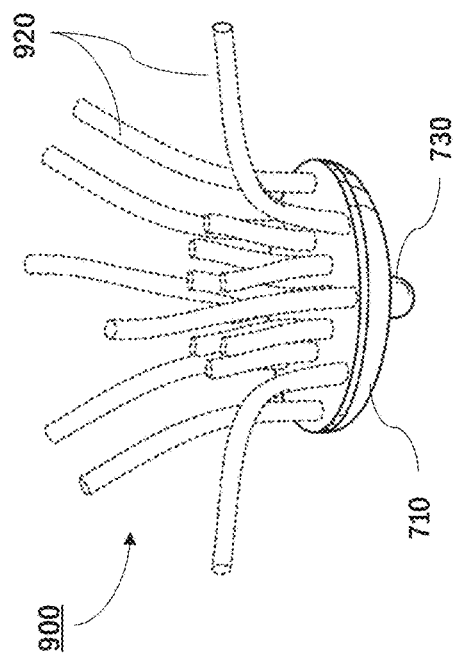
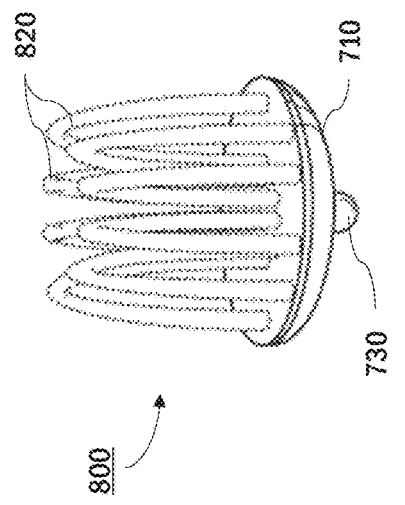
FIG. 7D  FIG. 7C  FIG. 7B  FIG. 7A  FIG. 8  FIG. 9

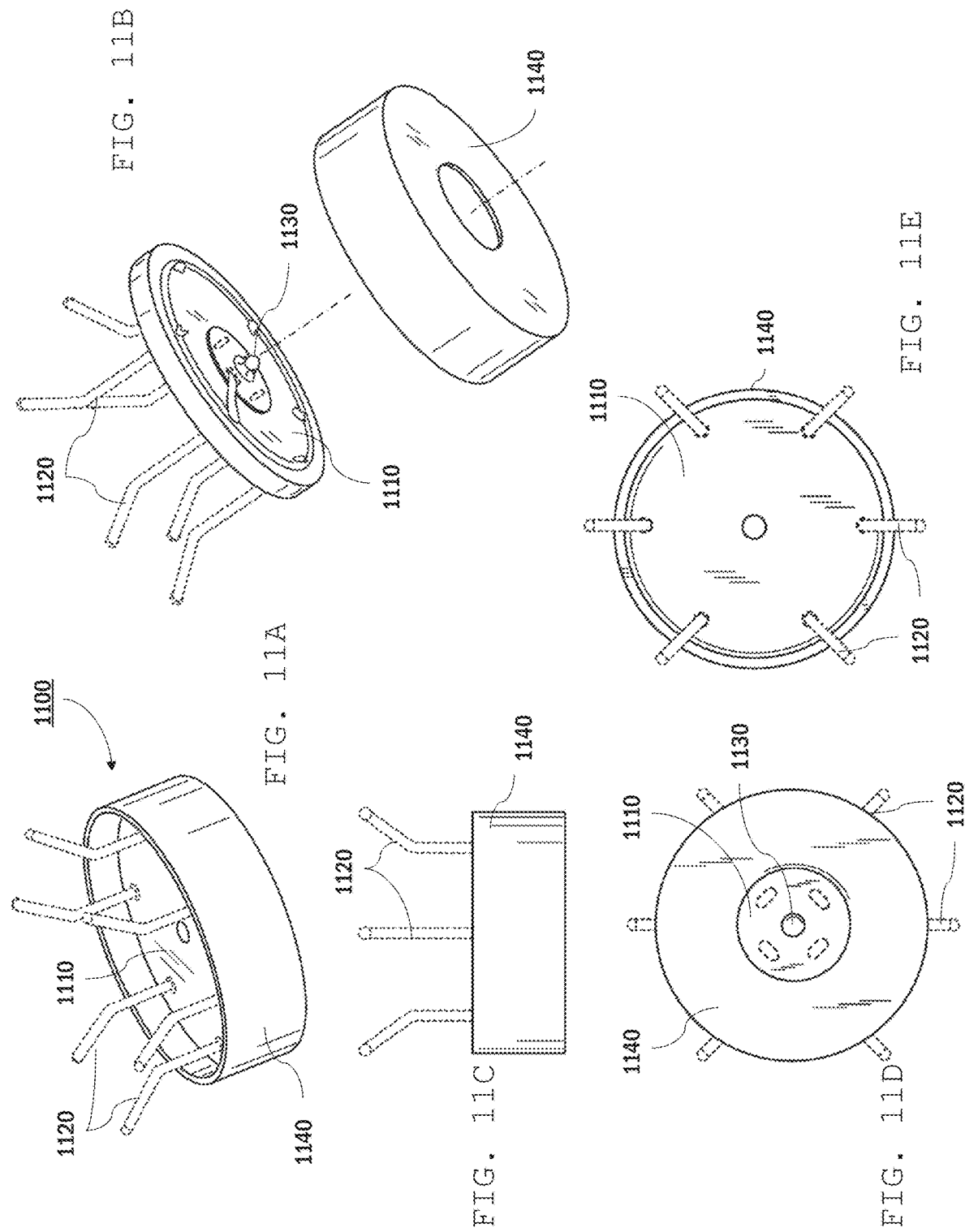

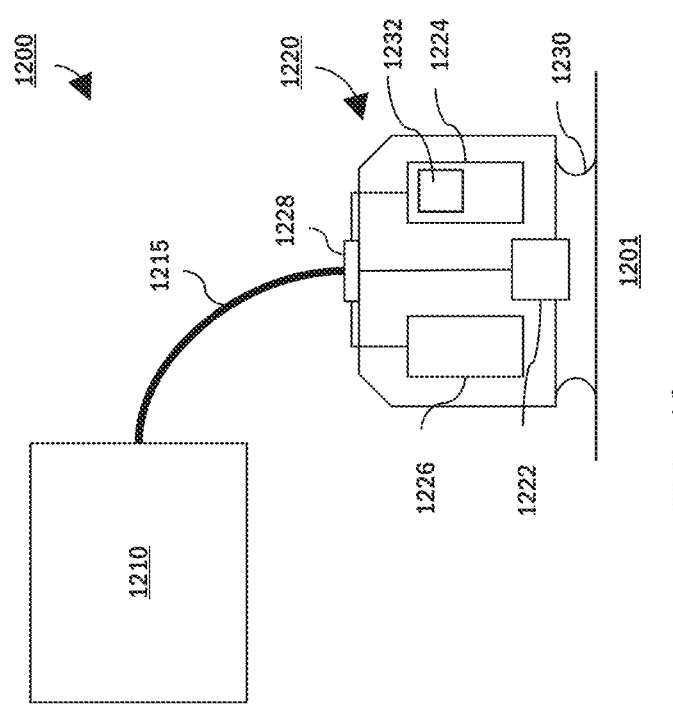

GEL-ASSISTED ELECTROENCEPHALOGRAM SENSOR ELECTRODE

FIELD

This specification relates generally to electroencephalogram (EEG) systems and more specifically to EEG systems and methods for using sensor electrodes with electrically conductive gel.

BACKGROUND

An electroencephalogram (EEG) is a measurement that detects electrical activity in a person's brain. EEG measures the electrical activity of large, synchronously firing populations of neurons in the brain with electrodes placed on the scalp.

EEG researchers have investigated brain activity using the event-related potential (ERP) technique, in which a large number of experimental trials are time-locked and then averaged together, allowing the investigator to probe sensory, perceptual, and cognitive processing with millisecond precision. However, such EEG experiments are typically administered in a laboratory environment by one or more trained technicians. EEG administration often involves careful application of multiple sensor electrodes to a person's scalp, acquiring EEG signals using specialized and complex equipment, and offline EEG signal analysis by a trained individual.

SUMMARY

This specification describes technologies for EEG signal processing in general, and specifically to systems and methods for using sensor electrodes with electrically conducting gel to facilitate continuous collection of brain activity data. These technologies generally involve an EEG system that is portable with easy to apply sensors. The sensors can automatically and/or continuously dispense conductive gel to a user's skin, e.g., on the user's scalp, in order to facilitate electrical contact between the sensor and the user's scalp, and thereby enhance collection of brain activity data. The sensors can also have a release mechanism that is configured to perform a release action to reduce the adhesion of the conductive gel and release the sensors that are bonded to the user's skin, e.g., on the user's scalp. Accordingly, an example EEG system, which is able to prompt, acquire, and process EEG signals in real time, and determine actions or behaviors desired by a user based on the EEG signals, can do so with reliable electrical contact of the sensor to the user's skin. Moreover, the sensors can be easily applied, easy removal, and minimal cleanup.

This specification also generally describes an EEG system, integrated with machine learning models, that provides cleaned EEG signals and can implement actions chosen by a user based on the EEG signals alone. For example, a user may be looking at a menu and create brain signals to select a menu item using only brain activity. The EEG system can receive EEG signals from the user's brain and determine which menu item the user intends to select based on the EEG signals. The EEG system uses the EEG signals as input to machine learning models and generates output including EEG signals and the user's selection.

In general, in a first aspect, the invention features an electroencephalogram sensor.

Other embodiments of this aspect include corresponding computer systems, apparatus, and computer programs recorded on one or more computer storage devices, each configured to perform the actions of the methods. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

The foregoing and other embodiments can each optionally include one or more of the following features, alone or in combination. In particular, one embodiment includes all the following features in combination.

An example method for analyzing electroencephalogram (EEG) signals includes: presenting information associated with two or more options to a user; receiving EEG signals from a sensor coupled to the user contemporaneously to the user receiving the information associated with the two or more options; processing the EEG signals in real time to determine which one of the options was selected by the user; and in response to determining which one of the options was selected by the user, selecting an action from one or more possible actions associated with the information presented to the user; and generating an output associated with the selected action.

In some embodiments, the generated output may include control signal for an electronic device.

In some embodiments, the steps of presenting, processing, and generating may be part of a closed-loop feedback system through which the user controls the electronic device. The information may be presented to the user using the electronic device. The electronic device may be selected from the group consisting of a networked device, a personal computer, a tablet computer, a mobile phone, and a wearable computer.

In some embodiments, information may be presented visibly or audibly to the user. The information may be presented based on an object detected in the user's environment. The object may be detected based using machine vision.

In some embodiments, processing the EEG signals may include cleaning the EEG signals in real time. Cleaning the EEG signals may include increasing a signal-to-noise ratio of the EEG signals. The EEG signals may be cleaned according to a machine learning model. The machine learning model may be a neural network or another artificial intelligence architecture. Processing the EEG signals may include performing mathematical transformations on the EEG signals in real time after cleaning the EEG signals to determine which of the options was selected by the user. The mathematical transformations may be performed according to a machine learning model. The machine learning model may be a neural network or other artificial intelligence architecture. The machine learning model may map a time series of values corresponding to an amplitude or change in amplitude of the EEG signal to an output variable corresponding to one of the options based on a mapping function. The mapping function may be determined by training the machine learning model.

In some embodiments, generating an output may include presenting the user with additional information associated with the selected action. The additional information associated with the selected action may be information associated with two or more further options.

In other embodiments, generating an output may include sending instructions over a network in communication with a processor used to process the EEG signals.

An example electroencephalogram system includes: a plurality of sensors for detecting electrical activity in a user's brain; a user interface configured to present information to the user; and a data processing apparatus in communication with the plurality of sensors and the user interface, the data processing apparatus comprising at least one computer processor and being programmed, during operation of the EEG system, to cause the EEG system to: prompt the user to select from two or more options; receive EEG signals from the plurality of sensors contemporaneously to the user receiving the information about the options; process the EEG signals in real time to determine which one of the options was selected by the user; in response to determining which one of the options was selected by the user, select an action from one or more possible actions associated with the information presented to the user; and generate an output associated with the selected action.

In some embodiments, the user interface is a component of an electronic device and the plurality of sensors and data processing apparatus are part of a closed-loop feedback system through which the user controls the electronic device. The electronic device may be selected from the group consisting of a networked device, a personal computer, a tablet computer, a mobile phone, and a wearable computer. The user interface may comprise an electronic display. The data processing apparatus may be programmed to process the EEG signals by cleaning the EEG signals in real time.

In some embodiments, the data processing apparatus may be programmed to process the EEG signals by performing mathematical transformations on the EEG signals in real time after cleaning the EEG signals to determine which one of the options was selected by the user. The mathematical transformations may be performed according to a machine learning model. At least one computer processor may perform both the EEG signal cleaning and the mathematical transformations.

In some embodiments, a bioamplifier may include the data processing apparatus. The bioamplifier may include an analogue-to-digital converter arranged to receive the EEG signals from the plurality of sensors and convert the EEG signals from analogue signals to digital signals. The bioamplifier may further include an amplifier arranged to receive the EEG signals from the analogue-to-digital converter and amplify the received EEG signals. The bioamplifier may include a housing containing the data processing apparatus and a power source.

In some embodiments, the user interface may include an electronic display. The user interface may include a camera.

In some embodiments, the system may include a networked computing device in communication with the user interface. In other embodiments, the system may include a mobile device, wherein the user interface and data processing apparatus are part of the mobile device.

In some embodiments, the plurality of sensors include an active sensor and a reference sensor. The plurality of sensors may be dry sensors.

In some embodiments, the system may include a wireless transceiver connecting the plurality of sensors with the data processing apparatus.

In some embodiments, generating the output includes providing one or more instructions to a computer program on a computer device in communication with the data processing apparatus. An example bioamplifier for analyzing electroencephalogram (EEG) signals includes: an input terminal for receiving an EEG signal from a plurality of sensors coupled to a user; an analogue-to-digital converter arranged to receive the EEG signal from the input terminal and convert the EEG signal to a digital EEG signal; a data processing apparatus arranged to receive the digital EEG signal from the analogue-to-digital converter and programmed to process, in real time, the digital EEG signal using a first machine learning model to generate a cleaned EEG signal having a higher signal-to-noise ratio than the digital EEG signal; a power source arranged to provide electrical power to the analogue-to-digital converter and the data processing apparatus; and a housing containing the analogue-to-digital converter, the data processing apparatus, the power source, and a housing containing the analogue-to-digital converter, the data processing apparatus, the power source, and the sensor input.

In some embodiments, the data processing apparatus may be further programmed to process, in real time, the cleaned EEG signal to determine a selection by the user of one of a plurality of options presented to the user.

In some embodiments, the data processing apparatus may be programmed to perform mathematical transformations on the cleaned EEG signal using a second machine learning model to determine a selection by the user of one of a plurality of options presented to the user.

In some embodiments, the data processing apparatus includes a computer processor programmed to implement both the first and second machine learning models.

In some embodiments, the second machine learning model may be a neural network or other artificial intelligence architecture.

The data processing apparatus may be programmed to synchronize the analysis with a presentation of the options to the user.

In some embodiments, the bioamplifier includes an output terminal for connecting the bioamplifier to a user interface and the data processing apparatus is programmed to synchronize the analysis with the presentation of the options to the user via the user interface.

In some embodiments, the user interface may be a component of an electronic device and the plurality of sensors and data processing apparatus are part of a closed-loop feedback system through which the user controls the electronic device. The electronic device may be selected from the group consisting of a networked device, a personal computer, a tablet computer, a mobile phone, and a wearable computer. The user interface may include an electronic display. The user interface may include a camera.

In some embodiments, the machine learning model may be a neural network or other artificial intelligence architecture.

In some embodiments, the bioamplifier may include an amplifier contained in the housing and arranged to receive the digital EEG signal from the analogue-to-digital converter and provide an amplified digital EEG signal to the data processing apparatus for processing.

In some embodiments, the power source may be a battery. The analogue-to-digital converter may be a 24 bit analogue-to-digital converter. The bioamplifier may have an input impedance of 10 MOhms or more. The input terminal may include a jack for receiving a connector from a lead. The input terminal may include a wireless transceiver for wirelessly receiving the EEG signal. An example method may include: receiving at least one EEG signal from a user via a plurality of sensors coupled to the user; amplifying, using a bioamplifier, the EEG signal from the plurality of sensors to provide an amplified EEG signal; processing, in real time, the amplified signal using a machine learning model that receives the amplified signal as input; and outputting a cleaned signal by the machine learning model, the cleaned signal having a higher signal-to-noise ratio than the at least one EEG signal received from the user.

In some embodiments, the method may further include processing, in real time, the cleaned EEG signal to determine a selection by the user of one of a plurality of options presented to the user.

In some embodiments, the method may further include sending a signal to an electronic device based on the selection determined from the cleaned EEG signal.

An example electroencephalogram (EEG) sensor includes: a housing defining a chamber capable of storing a gel, the housing including a first chamber wall and a second chamber wall on the opposite side of the chamber from the first chamber wall, the first and second chamber walls each including a corresponding access port located on a common axis extending through the housing; an electrically-conductive probe with a probe tip extending at least partially through the chamber along the axis, at least a portion of the probe tip being exposed to the chamber; an electrical terminal located at an outer surface of the second chamber wall, the electrical terminal being in electrical communication with the probe tip through the access port at the second chamber wall; and a compliant member mechanically coupled to the access port at the first chamber wall capable of compressing, thereby providing a dispense pathway from the chamber through the access port at the first chamber wall.

In some embodiments, the access port at the first chamber wall may include an aperture through the first chamber wall.

In some embodiments, the compliant member may be a spring element attached to the electrically-conductive probe. The spring may be a spiral spring arranged co-axially with the axis. The spring may be mechanically attached to the electrically-conductive probe. The spring and electrically-conductive probe may be arranged so that axial pressure is applied to the tip causing the tip to retract into the chamber and compressing the spring.

In some embodiments, the compliant member may be a semi-permeable element. The semi-permeable element may be a sponge. Compression of the sponge may increase a permeability of the gel through the sponge.

In some embodiments, an electrically-conducting material disposed on an outer surface of the first chamber wall. The electrical terminal may include a connector for connecting to an electrical lead.

In some embodiments, the first chamber wall may include one or more additional access ports each defining a corresponding dispense pathway.

An example apparatus includes the EEG sensor that includes a housing defining a chamber capable of storing a gel, the housing including a first chamber wall and a second chamber wall on the opposite side of the chamber from the first chamber wall, the first and second chamber walls each including a corresponding access port located on a common axis extending through the housing; an electrically-conductive probe with a probe tip extending at least partially through the chamber along the axis, at least a portion of the probe tip being exposed to the chamber; an electrical terminal located at an outer surface of the second chamber wall, the electrical terminal being in electrical communication with the probe tip through the access port at the second chamber wall; and a compliant member mechanically coupled to the access port at the first chamber wall capable of compressing, thereby providing a dispense pathway from the chamber through the access port at the first chamber wall. The apparatus also includes a pump in fluid communication with the chamber, the pump being arranged to apply pressure to a gel stored in the chamber.

In some embodiments, the pump may be configured to supply gel to the chamber. In other embodiments, the pump may be configured to supply pressured gas to the chamber. The pump may be a manual pump. The pump may be an electro-mechanical pump.

In some embodiments, the EEG sensor houses the pump. The pump may be in fluid communication with the chamber via a fluid channel.

An example apparatus includes the EEG sensor disclosed above, further comprising an actuator and a signal generator in communication with the actuator, wherein during operation the actuator cause the EEG sensor to dispense gel through the dispense pathway in response to a signal from the signal generator.

An example electroencephalogram system includes an EEG controller; and an EEG sensor including a contact surface, the contact surface comprising an electrically-conductive portion in communication with the EEG controller; and a sensor release element in communication with the EEG controller, the sensor release element being configured to perform, in response to a signal from the EEG controller, a release action to reduce adhesion of an electrically-conductive gel between the contact surface of the sensor and the user's skin.

In some embodiments, the sensor release element may include a heating element. Upon activation by the EEG controller, the heating element may be arranged to heat the electrically-conductive gel to a temperature that reduces adhesion of an adhesive in the electrically-conductive gel. Upon activation by the EEG controller, the heating element may be arranged to heat the electrically-conductive gel to a temperature that increase evaporation of the electrically-conductive gel relative to 98° F.

In some embodiments, the sensor release element may include a light emitting element. Upon activation by the EEG controller, the light emitting element may emit radiation having energy at a wavelength that reduces adhesion of adhesive in the electrically-conductive gel. The light emitting element may emit ultra-violet radiation.

In some embodiments, the sensor release element may include an actuator. Upon activation by the EEG controller, the actuator may change a shape of a surface of the EEG sensor to reduce adhesive forces between the sensor and the user's skin.

In some embodiments, the sensor release element includes a fluid dispense element. Upon activation by the EEG controller, the fluid dispense element may dispense fluid including a solvent, a diluent, a surfactant, or a reagent to the gel. The fluid may reduce adhesion of an adhesive in the electrically-conductive gel.

In some embodiments, the EEG sensor may include a hygroscopic material in contact with the gel. Upon activation by the EEG controller, the sensor release element may cause the hygroscopic material to release or absorb water to reduce adhesive forces between the sensor and the user's skin.

An example method includes: applying an electrically-conducting gel to skin on a user's scalp; adhering a sensor to the subject's scalp with the electrically-conducting gel, the sensor including a sensor release element; acquiring electroencephalogram (EEG) signals using the sensor; and after acquiring the EEG, causing the sensor release element to perform a release action to reduce adhesion of the electrically-conductive gel between the sensor and the user's skin.

In some embodiments, the release action may include heating the gel. In some embodiments, the release action includes delivering a release agent to the gel. The release agent may be a solvent, a reagent, or a surfactant. The release action may include changing a shape of a surface of the sensor.

Among other advantages, an example EEG sensor includes an auto-dispensing mechanism to automatically and/or continuously dispense conductive gel to a user's skin in order to achieve sufficient electrical contact to collect brain activity data. Exemplary EEG sensors can dispense a small volume of conductive gel in controlled amounts so that the EEG sensor can maintain electrical contact with a user's skin for a prolonged period of time.

Conventionally, during prolonged use, the applied conductive gel may dry out, resulting in a corresponding reduction in the electrical contact and possible user discomfort. Moreover, manual application of the gel often results in wasteful and messy application of the gel in larger volumes and over a larger area than necessary to provide the desired electrical connection. Unlike conventional sensors, exemplary sensors' auto-dispense mechanisms apply conductive gel only to the area of the user's scalp where electrical contact is desired, avoiding waste and mess associated with manual application.

In certain embodiments, highly adhesive gel can be used, maintaining contact and position on the user's skin during prolonged use. For example, adhesive-containing gel can be used. In some embodiments, sensors can include a sensor release element to reduce the adhesion of the conductive gel and facilitate clean, comfortable release of the sensor from the user's skin. This sensor release element within the EEG sensor quickly and easily delaminates the sensor from the user without requiring manual intervention.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

FIG. 7A is a perspective view of an embodiment of a sensor electrode including multiple wire loops.

FIG. 7B is a side view of the sensor electrode shown in FIG. 7A.

FIG. 7C is a top view of the sensor electrode shown in FIG. 7A.

FIG. 7D is a bottom view of the sensor electrode shown in FIG. 7A.

FIG. 8 is a perspective view of another embodiment of a sensor electrode including multiple wire loops.

FIG. 9 is a perspective view of an embodiment of a sensor electrode that includes wires of differing lengths.

FIG. 11A is a perspective view of an embodiment of a sensor electrode that includes a protective collar.

FIG. 11B is an exploded perspective view of the sensor electrode shown in FIG. 11A.

FIG. 11C is a side view of the sensor electrode shown in FIG. 11A.

FIG. 11D is a bottom view of the sensor electrode shown in FIG. 11A.

FIG. 11E is a top view of the sensor electrode shown in FIG. 11A.

FIG. 12 is an EEG system with an enlarged view of a sensor.

Like reference numbers and designations in the various drawings indicate like elements.

DETAILED DESCRIPTION

Figure 1:
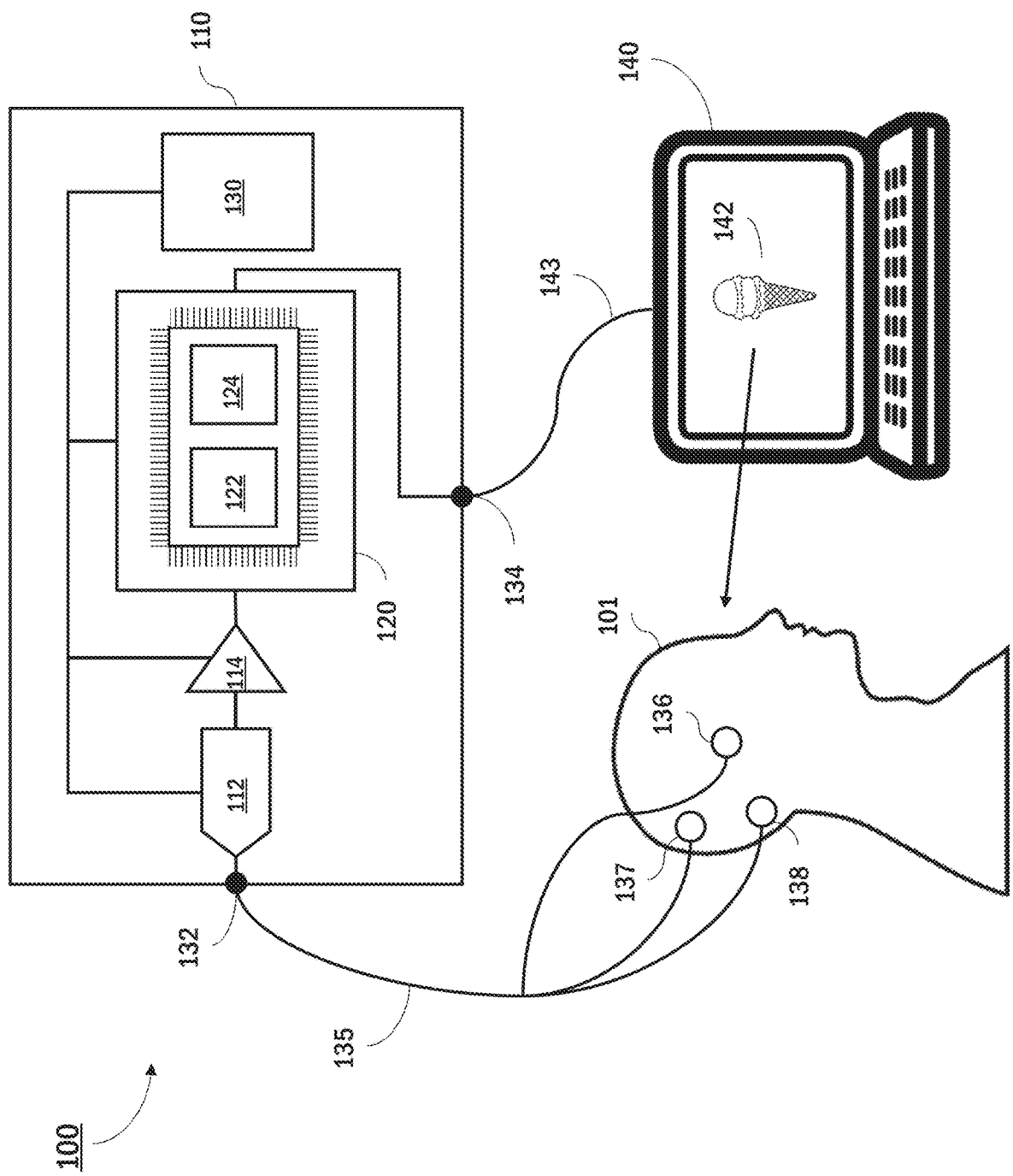
FIG. 1 is a schematic diagram of an embodiment of an EEG system.

Referring to FIG. 1, an EEG system 100 features a portable bioamplifier 110 that collects and analyzes EEG signals from a user 101 using electrode sensors 136, 137, and 138 attached to user 101's scalp. Bioamplifier 110 is in communication with a personal computer 140 which displays information 142—in this instance an image of an ice cream cone—to user 101. Bioamplifier 110 synchronously collects EEG signals from user 101 while displaying information 142 and analyzes the EEG signals, interpreting in real time user 101's brain activity responsive to viewing the information.

In certain embodiments, bioamplifier 110 is a high-impedance, low-gain amplifier with a high dynamic range. The bioamplifier impedance may be, for example, higher than 10 megaohms (e.g., 12 M$\Omega$ or more, 15 M$\Omega$ or more, 20 M$\Omega$ or more) with a maximum gain of 24$x$ amplification. The dynamic range of bioamplifier 110 should be sufficient to acquire the entire voltage range of typical EEG signals (e.g., 0.1 to 200 µV over frequency ranges of 1 to 100 Hz). As a portable unit, bioamplifier 110 is housed within a compact, robust casing, providing a package that can be readily carried by user 101, sufficiently robust to remain functional in non-laboratory settings.

Electrode sensors 136, 137, and 138 may be dry sensors or may be placed in contact with the user's scalp using a gel. The sensors can be secured in place using, for example, adhesive tape, a headband, or some other headwear. One of sensors 136, 137, and 138 is an active sensor. Generally, the active sensor's location on the user's scalp depends on the location of brain activity of interest. In some implementations, the active sensor is placed at the back of the user's head, at or close to the user's inion. Another one of the sensors is a reference sensor. The EEG signal typically corresponds to measured electrical potential differences between the active sensor and the reference sensor. The third sensor is a ground sensor. Typically, the ground sensor is used for common mode rejection and can reduce (e.g., prevent) noise due to certain external sources, such as power line noise. In some implementations, the ground and/or reference sensors are located behind the user's ears, on the user's mastoid process.

Bioamplifier 110 includes jacks 132 and 134 for connecting leads 135 and 143 to the electrode sensors and personal computer 140, respectively. Bioamplifier 110 further includes an analogue-to-digital converter 112, an amplifier 114, and a processing module 120. Although depicted as a single analogue-to-digital converter and a single amplifier, analogue-to-digital converter 112 and amplifier 114 may each have multiple channels, capable of converting and amplifying each EEG signal separately. A power source 130 (e.g., a battery, a solar panel, a receiver for wireless power transmission) is also contained in bioamplifier 110 and is electrically connected to ADC 112, amplifier 114, and processing module 120. In general, analogue-to-digital converter 112 and amplifier 114 are selected to yield digital signals of sufficient amplitude to be processed using processing module 120.

Processing module 120 includes one or more computer processors programmed to analyze and clean amplified EEG signals received from amplifier 114 in real time. The computer processors can include commercially-available processors (e.g., a raspberry pi micro-controller) and/or custom components. In some embodiments, processing module 120 includes one or more processors custom designed for neural network computations (e.g., Tensor Processing Unit from Google or Intel Nervanna NNP from Intel Corp.). Generally, processing module 120 should include sufficient computing power to enable real time cleaning and analysis of the EEG signals.

The components of processing module 120 are selected and programmed to include two machine learning (ML) models: a ML cleaning model 122 and a ML two-choice decision model 124. ML cleaning model 122 receives raw EEG signals from amplifier 114 and, by application of a machine learning algorithm, cleans the signals to reduce noise. Thus, ML cleaning model 122 outputs cleaned EEG signals that have a reduced signal-to-noise ratio as compared with the input signals. Cleaning the EEG signal includes various operations that improve the usability of the signal for subsequent analysis, e.g., by reducing noise in the EEG signal. For example, cleaning the EEG signal can include filtering the signal by applying a transfer function to input data, e.g., to attenuate some frequencies in the data and leave others behind. Other signal cleaning operations are also possible. For example, signals can be cleaned using a neural network. Cleaning can also include operations to improve signal quality besides removal of undesirable frequencies. For instance, cleaning can include removing blinks, which digital filtering alone does not do.

Figure 2:
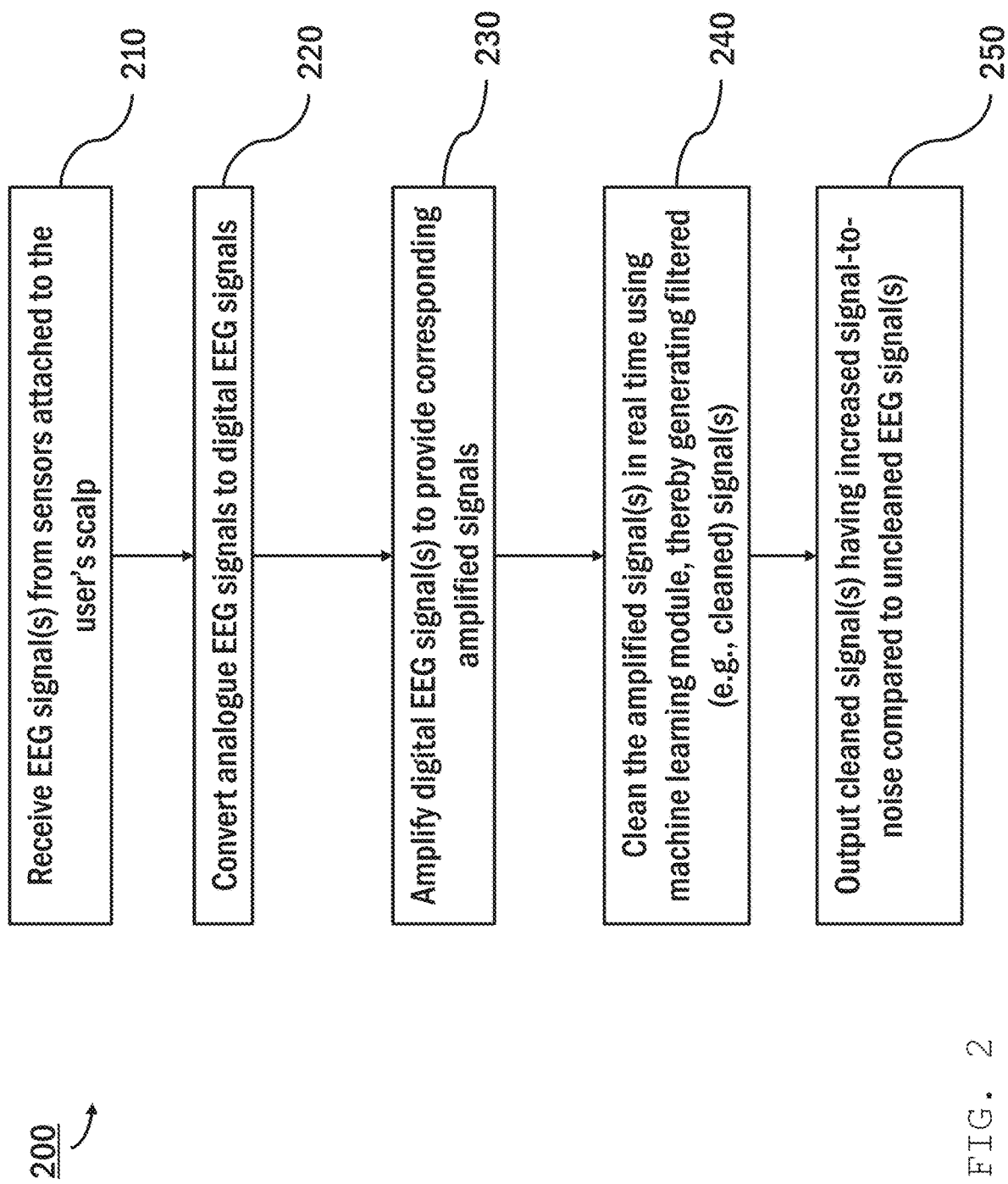
FIG. 2 is a flowchart showing aspects of the operation of the EEG system shown in FIG. 1

Referring to FIG. 2, the process of digitizing, amplifying, and cleaning an EEG signal is shown in a flowchart 200. An EEG signal, e.g., a time-varying voltage differential between a voltage measured using an active sensor and a reference sensor, is received by a bioamplifier (e.g., bioamplifier 110) from the sensors attached to the user's scalp (step 210). The frequency at which the sensor voltage is sampled should be sufficient to capture voltage variations indicative of the brain activity of interest (e.g., between 0.1 and 10 Hz, at 10 Hz or more, at 50 Hz or more, at 100 Hz or more). An ADC (e.g., ADC 112) converts the signal from an analogue signal to a digital signal (step 220) and sends the digital signal to an amplifier (e.g., amplifier 114). The digital EEG signal is then amplified (e.g., by amplifier 114) (step 230), and the amplified signal sent to a processor (e.g., processing module 120). The processor (e.g., processing module 120), in real time, cleans the amplified signal using a machine learning model (e.g., ML model 122), thereby generating a filtered (e.g., cleaned) signal (step 240), and outputs the cleaned signal having increased signal-to-noise compared to an uncleaned EEG signal (step 250).

In general, any of a variety of ML models suitable for signal processing can be used to clean the amplified EEG signal. In many cases, the ML model is a neural network, which is an ML model that employs one or more layers of nonlinear units to predict an output for a received input. Some neural networks are deep neural networks that include two or more hidden layers in addition to the input and output layers. The output of each hidden layer is used as input to another layer in the network, i.e., another hidden layer, the output layer, or both. Some layers of the neural network generate an output from a received input, while some layers do not (remain "hidden"). The network may be recurrent or feedforward. It may have a single output or an ensemble of outputs; it may be an ensemble of architectures with a single output or a single architecture with a single output.

A neural network for a machine learning model (e.g., ML model 122) can be trained on EEG-specific data in order to distinguish between actual, usable data and noise. The ML model can be trained to classify artifacts in the EEG and to deal with EEG segments that have different types of noise in different ways. For example, if the network recognizes a vertical eye movement (a blink) it could attempt to remove the blink using a different approach than it would use if it recognized a horizontal eye movement. The ML model can be trained to clean data to an arbitrary level of precision—that is, it can clean up the raw data a little bit or a lot but there is no theoretical limit as to how closely the ML model can reproduce the type of clean data it was trained on. The level of cleaning that the ML model does is dependent only on time and the architecture of the model, that is, there is no theoretical maximum amount of possible cleaning.

EEG signals, even under controlled conditions, may contain significant noise, e.g., due to biological and/or electrical sources. The propensity for noise is further increased outside of a well-controlled laboratory environment. Accordingly, ML-based noise reduction may be particularly beneficial in providing usable EEG data in real time in real world (i.e., outside of a well-controlled environment) conditions.

As noted previously, a processor (e.g., processing module 120) includes a machine learning two-choice decision model (e.g., ML two-choice decision model 124) for analyzing cleaned EEG signals that output from a machine learning cleaning model (e.g., ML cleaning model 122). The two-choice model interprets a response of a user (e.g., user 101) to information (e.g., information 142) presented via a computer (e.g., computer 140). A user's response may be a selection of one choice among a finite set, e.g., two or more, of choices presented to the user. The two-choice model associates one of two binaries with information (e.g., information 142), such as interest (e.g., acceptance of an option) of the user in the information, or disinterest (e.g., rejection of an option).

Figure 3:
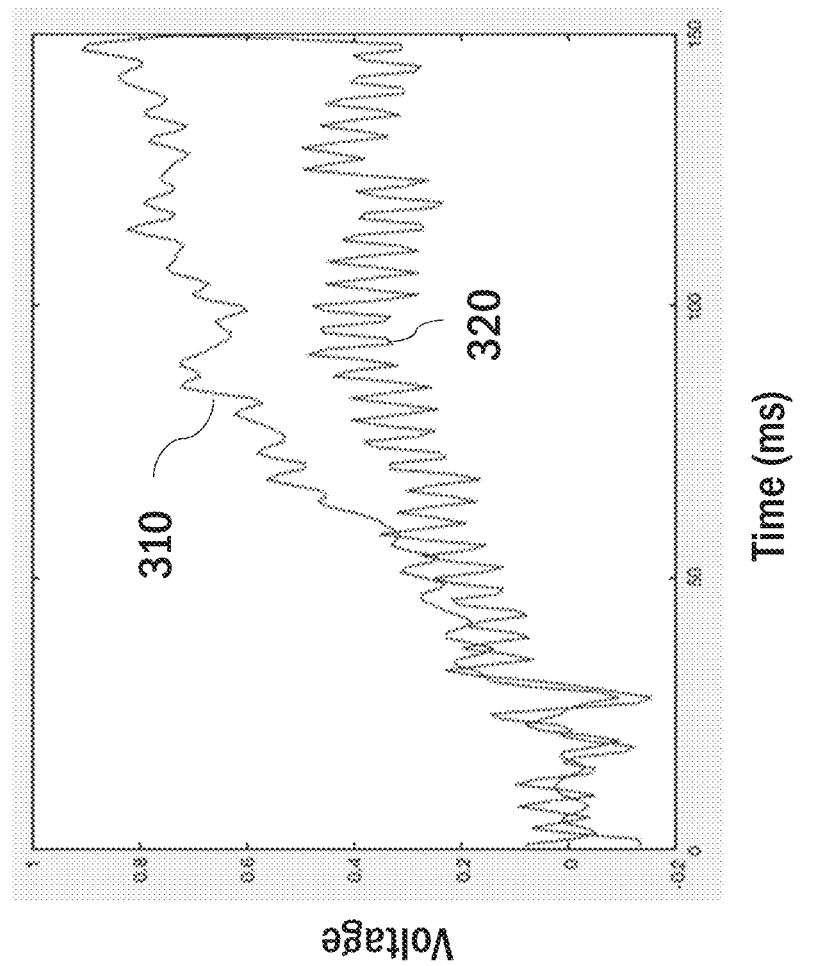
FIG. 3 is a plot comparing two EEG signals for analysis using the system in FIG. 1.

In general, various parameters of the cleaned EEG signal can be used to determine the user's response (e.g., the user's choice selection). Often, these parameters include the amplitude of the response amplitude over a relevant time period (e.g., within about 500 ms of being presented with information 142). This is illustrated in the plot shown in FIG. 3, for example, which compares two EEG signals corresponding to interest (trace 310) and disinterest (trace 320) in information presented to the user. After an initial latency of approximately 50 ms, trace 310 has a significantly larger amplitude than trace 320. A machine learning model (e.g., ML model 124) associates the higher amplitude with the user's interest, and returns this information to a computer (e.g., computer 140).

Figure 4:
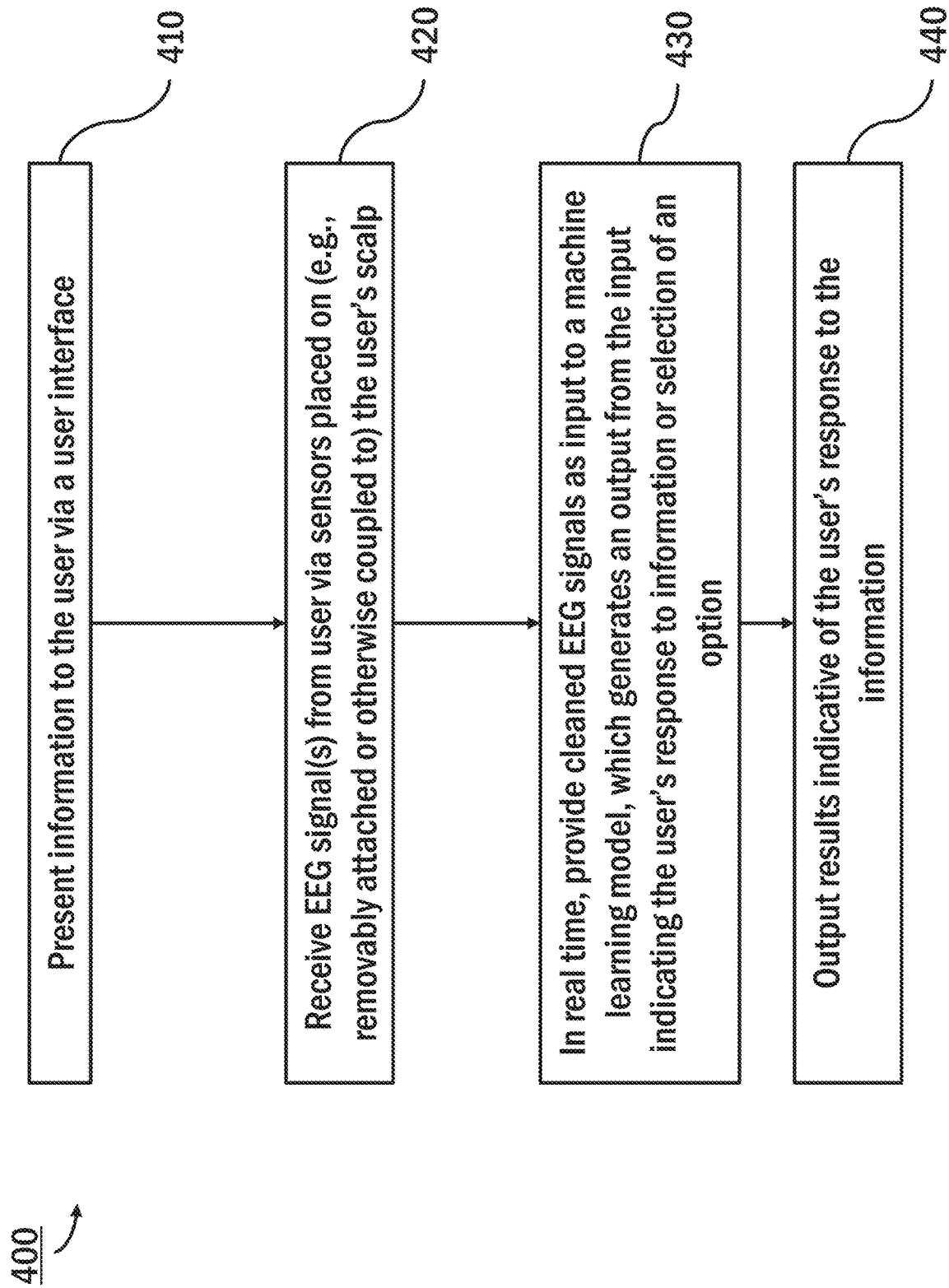
FIG. 4 is a flowchart showing other aspects of the operation of the EEG system shown in FIG. 1.

This process is illustrated by flowchart 400 shown in FIG. 4. In step 410, a system (e.g., system 100) presents information (e.g., information 142) to a user (e.g., user 101) via a user interface, for example, provided by a personal computer (e.g., personal computer 140). The system (e.g., system 100) receives EEG signals from the system's sensors placed on (e.g., removably attached or otherwise coupled to) the user's scalp (step 420). The system (e.g., system 100) amplifies and cleans the signals as described above using an amplifier and a machine learning model (e.g., ML model 122). The system (e.g., system 100) then provides the cleaned EEG signals as input to a machine learning model (e.g., ML model 124), which generates an output from the input indicating the user's response to information (e.g., information 142) or selection of an option (step 430). The system provides input and generates output in real-time to feed a closed loop. In embodiments, signal analysis involves correlating the cleaned EEG signal to the presentation of information to the user (e.g., by matching a time-stamp associated with signal to the time of presentation) and observing the time-varying amplitude of the signal associated with the user's brain activity responsive to the information. The system can decompose the signal into a time series of signal amplitude and/or change in signal amplitude and perform mathematical operations on the time series to determine the user's intent. For example, the mathematical operations can associate a change in signal amplitude above a certain threshold and within a certain time (e.g., with 50 ms or less) of presenting the user with the information with a particular intention (e.g., an affirmative response) and a change in signal amplitude below the threshold with the opposite intention (e.g., a negative response). The threshold amplitude and/or response time can be determined by training the ML model.

The system (e.g., system 100) then outputs results indicative of the user's response to the information (step 440). The user's response to the information may be a selection among multiple choices. For example, the user may be presented with a menu of options to order for dinner. The user may respond with EEG signals that the system can process to determine the user's dinner choice. The system can then output the selected dinner choice of the user.

In some embodiments, a bioamplifier (e.g., bioamplifier 110) can relay the results of two-choice decision model analysis to another device (e.g., personal computer 140), which may take certain actions depending on the results. Examples are described below.

In some embodiments, the cleaning and analysis processing occurs on the same processing module (e.g., using the same processor, e.g., the same processor core), the system does not need to send the signals across a network and therefore does not incur added data processing latency of network connections or bandwidth restrictions. The system executes calculations as soon as the amplified signal is ready for processing, providing a very low lag response to the user.

Moreover, the system can operate as a closed-loop system. For example, the bioamplifier and other device (e.g., personal computer 140) operate using feedback in which the system regulates presentation of information to the user by the device based on the analysis of the user's prior or contemporaneous EEG signals. For instance, the device can present the user with a choice between two or more different options and, based on the user's selection as interpreted from the associated EEG signals, present subsequent choices to the user associated with the user's prior choice.

In some embodiments, the system (e.g., system 100) can use the received EEG signals from the user's brain activity to determine a user's selection among the finite set of possibilities and subsequently perform an action based on the user's selection without requiring the user to provide more input than the brain activity signals. In order to determine the correct action to execute, a machine learning model (e.g., ML model 124) takes EEG signals as input and classifies the EEG signals according to the user's intended action. This is achieved by processing the cleaned EEG input to the machine learning model (e.g., ML model 124) through the hidden layers of the model and performing machine classification. This may involve, for example, feature extraction or successive nonlinear recordings.

Essentially, the cleaned data is presented to the machine learning model (e.g., ML model 124) and then the machine learning model (e.g., ML model 124) performs a number of mathematical transformations of the cleaned data in order to produce an output that reflects the intention of the user as encoded in the EEG data. The ML model is able to do this because it has been extensively trained, prior to interaction with the user, on what types of EEG signals correspond to what types of responses (e.g., selections by the user).

In general, a variety of neural networks can be used to analyze and classify the data. For example, the neural network can be a convolutional neural network model, a support vector machine, or a generative adversarial model. In some implementations, lower dimensional models, e.g., a low featural multilayer perceptron or divergent autoencoder can be implemented. The minimum number of features that can be used to achieve acceptable accuracy in decoding the user's intention is preferred for computational simplicity. The optimized models may be trained or simulated in constrained computing environments in order to optimize for speed, power, or interpretability. Three primary features of optimization are 1) the number of features extracted (as described above), 2) the "depth" (number of hidden layers) of the model, and 3) whether the model implements recurrence. These features are balanced in order to achieve the highest possible accuracy while still allowing the system to operate in near real time on the embedded hardware.

In some embodiments, the machine learning model (e.g., ML model 124) uses sub-selection in which the model only compares the current user's brain activity with other user samples that are most similar to that of the user in order to determine the user's selection. Similarity to other users can be operationalized with standard techniques such as waveform convolution and normalized cross correlation. Alternatively, the machine learning model (e.g., ML model 124) compares the user's brain activity to that of all brain activity present in a large dataset. The dataset may contain brain activity samples from one or more other users. Samples for comparison are drawn either from 1) a data system's internal user data or 2) data collected from external users who have opted-in to having their data be included in the comparison database. All samples are anonymized and are non-identifiable.

To train the machine learning model (e.g., ML model 124), a system (e.g., system 100) can present a user with a choice problem, e.g., a two-choice problem, using a display on a personal computer (e.g., computer 140) or some other interaction element. In some implementations, the system (e.g., system 100) provides the user with one object at a time, e.g., for 500 milliseconds, with random jitter, e.g., between 16 and 64 milliseconds, added between objects. Each image shown to the user is either an image of a first type of object or an image of a second type of object. Prior to displaying any images, the user is told to pay particular attention to the first type of object, e.g., by counting or some other means. While the system (e.g., system 100) is presenting images to the user, it differentiates EEG signals between when the user is paying particular attention to images of the first type of object and when the user is not paying as close of attention to images of the second type of object.

For example, the system (e.g., system 100) presents the user with sequence of images showing one of two different objects (e.g., a rabbit or a squirrel). Prior to displaying images, the user is told to pay particular attention to images of squirrels only, and to count the squirrels. As each image displays, the system (e.g., system 100) records the user's brain activity and determines a difference between when the user views an image of a rabbit and when the user views an image of a squirrel. This difference is attainable because 1) the squirrels are task-relevant (to the task of counting squirrels) and the rabbits are not and 2) the squirrel-counting task requires an update of working memory (i.e., the number of squirrels that have been viewed) each time a squirrel appears. These cognitive processes are reflected in relatively large signals measurable by the EEG system and separable by the ML model.

In some embodiments, the machine learning model (e.g., ML model 124) can be trained using equal numbers of objects so that the model does not learn the true population frequency distribution of the objects in the user's world, which may impair the model's ability to distinguish between the user's choices. For example, the system may be trained with equal numbers of squirrels and rabbits, though most users encounter squirrels more often than rabbits.

After collecting samples from the user, the system (e.g., system 100) classifies the user's EEG signals to distinguish between EEG signals elicited when the user is focused on an image (e.g., views the squirrel in the example above) and when the user is not (e.g., the rabbit). This is accomplished by the machine learning model (e.g., ML model 124). Prior to being passed to the ML system, the signals may be pre-processed, such as by boxcar filtering, range-normalization, or length normalization. The pre-processed signals are then passed to the machine learning model (e.g., ML system 124) for classification. The classification may be implemented in either a single-model fashion (i.e., classification is done by a single model) or in an ensemble-model fashion (i.e., a number of different types of models all make a classification and then the overall choice is made by a vote). In some implementations, the user samples can be added to the dataset in a database accessible to the system (e.g., system 100) and used to train subsequent neural network models.

Once the model is trained broadly across multiple functional objects, tasks, and people, the system can use the ML model on any person for any decision task without further training. The more similar the new decision task is to the trained task, the more effective this transfer will be.

ML models can be trained on various characteristics of the user. For example, in some implementations, models may be trained on a specific age group, e.g., over 40 or under 20. The model may take into account a user's age and choose user samples in the same age range or choose from a subset of user samples in the database. As described above, the database will consist of both internal data and data from external users who have opted-in to their data being included in the comparison database. All samples are anonymized and non-identifiable. Individuals will have the option to include not only their EEG data, but other demographic data such as age and gender. System 100 can then use the trained model in real-life scenarios to distinguish between a selection event by the user and rejection.

In general, an EEG system (e.g., EEG system 100) can present a user (e.g., user 101) with choices among a finite set, e.g., two or more, of possibilities, determine the choice that the user (e.g., user 101) has made based on EEG signals from brain activity, and then perform further actions based on the user's choice. As a result, the user (e.g., user 101) can cause the system (e.g., system 100) to perform certain actions without any physical action beyond having the user view the choices on a display and generate brain activity from a selection of the viewed choices.

For example, the user (e.g., user 101) can choose a contact from a list of multiple contacts and place a phone call the chosen contact using only the user's brain activity. To perform this activity, the EEG system (e.g., EEG system 100) sequentially presents the user (e.g., user 101) with a list of contacts via a computer (e.g., computer 140) and identifies a selection from the list based on received EEG signals from the user's corresponding brain activity. Next, the system (e.g., system 100) presents the user (e.g., user 101) with options for contacting the selected contact, e.g., call, text, share, or email. Again, the system identifies the user's selection based on received EEG signals corresponding to the user's brain activity representing a selection of an option. The system (e.g., system 100) then performs the call or provides instructions to a telephone to make the call.

Figure 5:
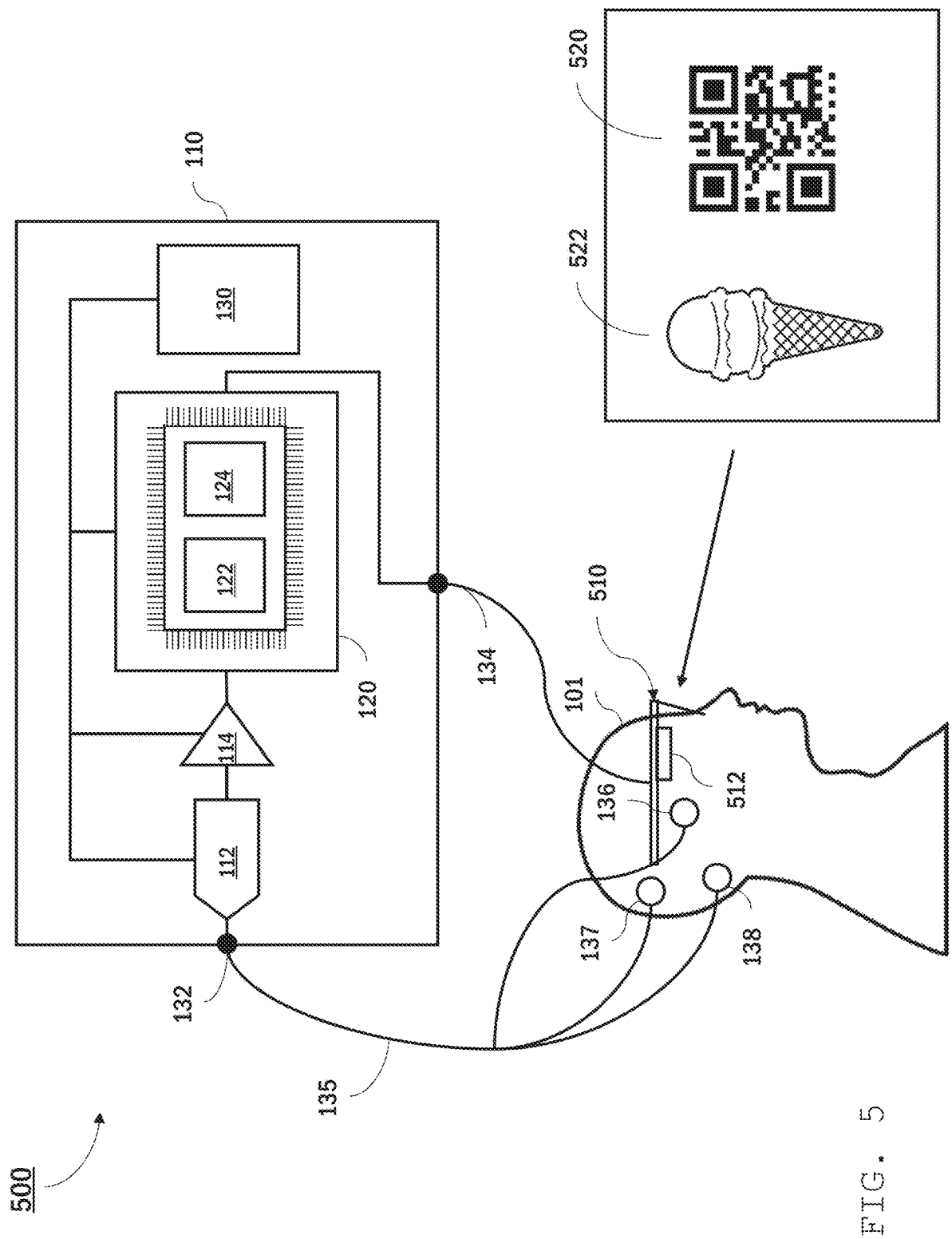
FIG. 5 is a schematic diagram of an embodiment of an EEG system that features a head-mounted camera.

While bioamplifier 110 is interfaced with personal computer 140 in system 100, other configurations are also possible. Referring to FIG. 5, for example, an EEG system 500 includes bioamplifier 110 interfaced with a head-mounted camera system 510 which is arranged to track user 101's field of view. Camera system 510 includes a camera 512 and onboard image processing for analyzing images captured by the camera of user 101's field of view. For example, EEG system 500 is configured to facilitate user 101's interaction with an object 522 associated with a quick response (QR) code 520 (as illustrated) or bar codes, NFC tags, or some other identification feature readily identifiable using machine vision.

An EEG system (e.g., system 500) analyzes EEG signals from a user (e.g., user 101) associated with brain waves responsive to a viewing object (e.g., viewing object 522) synchronously with reading a QR code (e.g., QR code 520). The analysis returns one of two binary choices, which the system associates with the viewing object (e.g., object 522) based on the system viewing the QR code (e.g., QR code 520).

Figure 6:
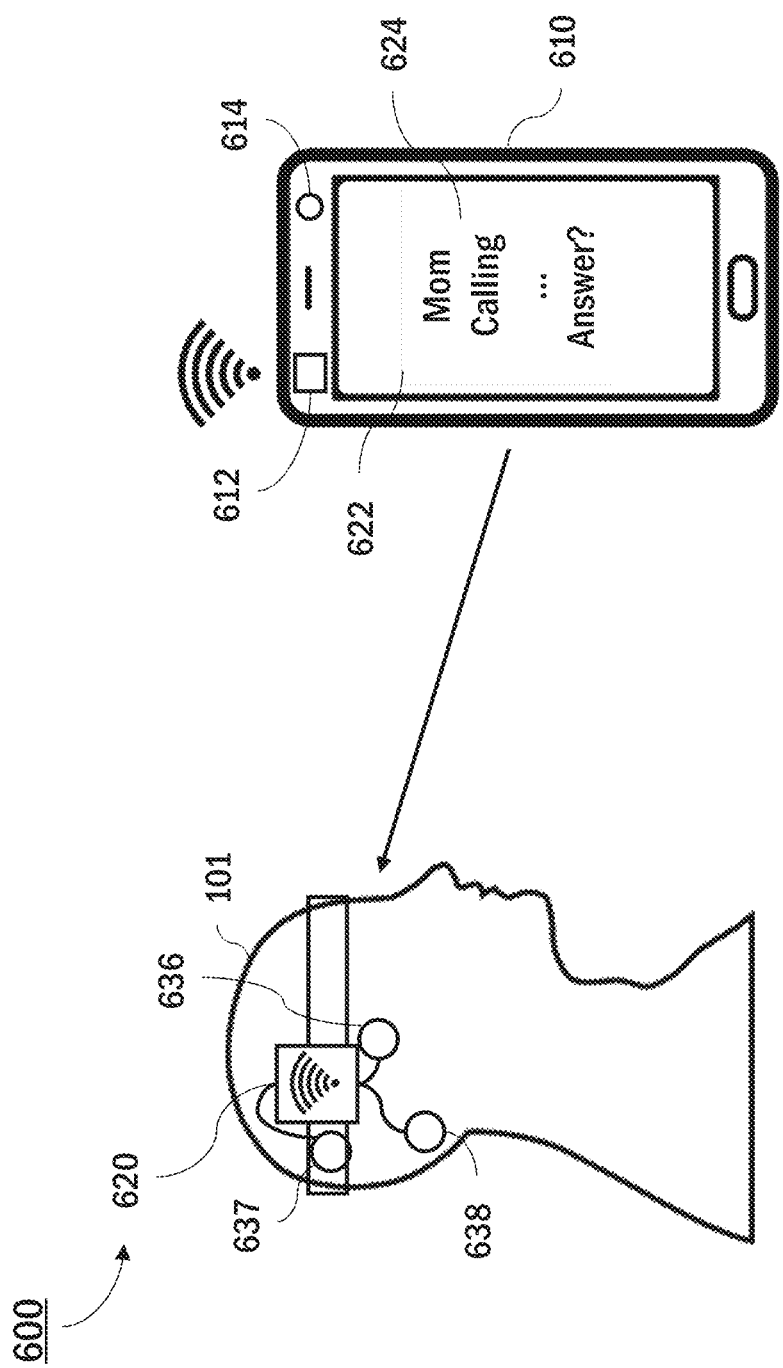
FIG. 6 is a schematic diagram of another embodiment of an EEG system that features a mobile phone and a wireless connection to the system's sensor electrodes.

While the systems described above both feature a portable bioamplifier (i.e., bioamplifier 110), that connects with either a computer or other interface, other implementations are also possible. For example, the components of a bioamplifier (e.g., bioamplifier 110) can be integrated into another device, such as a mobile phone or tablet computer. Moreover, while the foregoing systems includes sensors that are connected to the portable bioamplifier using leads, other connections, e.g., wireless connections, are also possible. Referring to FIG. 6, for instance, an EEG system 600 includes a mobile phone 610 and a head-mounted sensor system 620. The cleaning and analysis functions of the components of portable bioamplifier 110, personal computer 140, and/or camera system 510 described above are all performed by mobile phone 610 alone, or in conjunction with cloud-based computer processors. Mobile phone 610 includes a wireless transceiver 612, a display 622, and a camera 614.

Sensor system 610 includes a transceiver unit 620 and sensors 636, 637, and 638 connected to the transceiver unit. The sensors measure EEG signals as described above, but the signals are related to receiver 612 using a wireless signal transmission protocol, e.g., Bluetooth®, near-field communication (NFC), or some other short-distance protocol.

During operation, a mobile phone (e.g., mobile phone 610) displays information (e.g., information 624) to a user (e.g., user 101) on a display (e.g., display 622) and, synchronously, receives and analyzes EEG signals from a transceiver unit (e.g., transceiver unit 620). Based on the EEG signal analysis, the mobile phone (e.g., mobile phone 610) can take certain actions related to the displayed information. For instance, the phone can accept or reject phone calls based on the EEG signals, or take some other action.

Alternatively, or additionally, a user (e.g., user 101) can use a camera (e.g., camera 614) to capture information in their environment (e.g., to scan a QR code) while the phone receives and analyzes their associated brain waves.

In general, the EEG systems described above can use a variety of different sensors to obtain the EEG signals. In some implementations, the sensor electrodes are "dry" sensor which feature one or more electrodes that directly contact the user's scalp without a conductive gel. Dry sensors can be desirable because they are simpler to attach and their removal does not involve the need to clean up excess gel. A sensor generally includes one or more electrodes for contacting the user's scalp.

Referring to FIGS. 7A-7D, for example, a sensor 700 includes multiple wire loop electrodes 720 mounted on a base 710, and a press stud electrode 730 on the opposite side of base 710 from wire loop electrodes 720. Wire loop electrodes 720 are bare electrically-conducting wires that are in electrical contact with metal press stud 730. During use, a user can position sensor 700 in their hair with the top of wire loop electrodes contacting their scalp. A lead, featuring female press stud fastener, is connected to press stud 730, connecting sensor 700 to a bioamplifier or transceiver. The multiple loop electrodes provide redundant contact points with the user's scalp, increasing the likelihood that the sensor maintains good electrical contact with the user's scalp.

As is apparent in FIG. 7C (top view), sensor electrode 700 includes a total of eight wire loop electrodes arranged symmetrically about an axis. More generally, the number of wire loop electrodes can vary as desired. The length of the wire loop electrodes (from base to tip) can also vary as desired. For instance, a user with long hair may select a sensor with longer wire loops than a user with shorter hair. FIG. 8, for example, shows another sensor electrode 800 similar to sensor electrode 700 but with shorter wire loop electrodes 820. In general, the loop electrodes can have a length from about 1 mm to about 15 mm.

FIG. 9 shows yet a further sensor electrode 900 that includes multiple wire electrodes 920. Wire electrodes 920 can be sufficiently flexible so that the user can bend them to provide optimal contact with the scalp. Each wire electrode 920 can have the same length, or the lengths of the wires can vary.

Figure 10A:
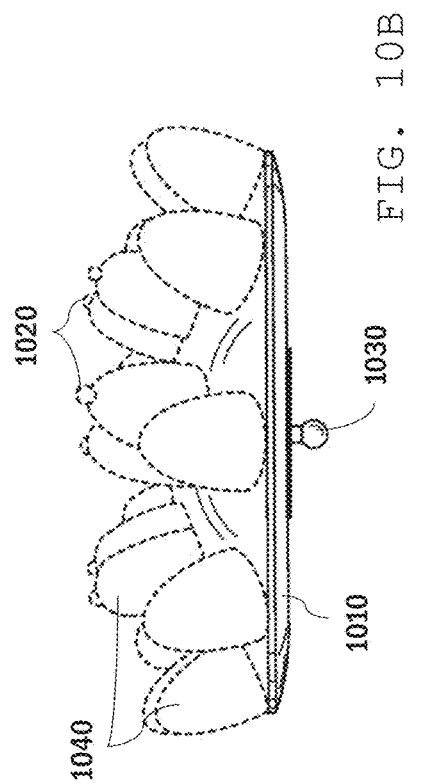
FIG. 10A is a perspective view of an embodiment of a sensor electrode that includes multiple protuberances.
Figure 10B:
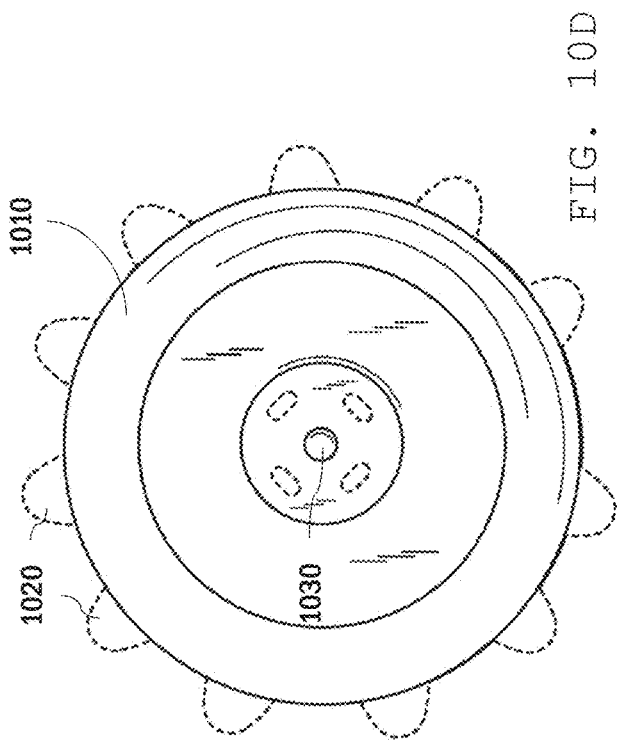
FIG. 10B is a side view of the sensor electrode shown in FIG. 10A.
Figure 10C:
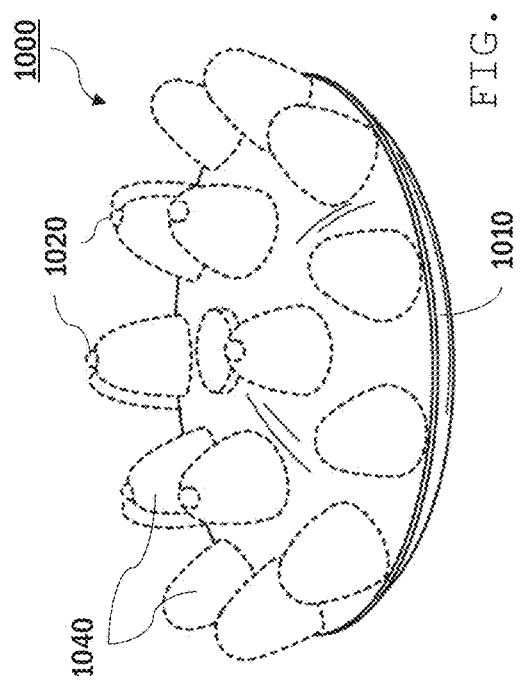
FIG. 10C is a top view of the sensor electrode shown in FIG. 10A.
Figure 10D:
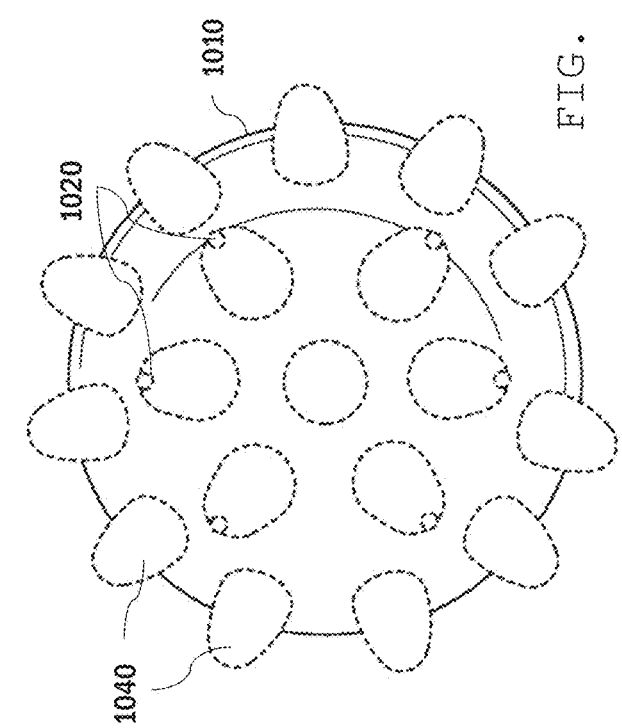
FIG. 10D is a bottom view of the sensor electrode shown in FIG. 10A.

Other dry sensor designs are also possible. For example, referring to FIGS. 10A-10D, a sensor electrode 1000 features multiple protuberances 1040 supported by a base 1010. The protuberances are formed from a relatively soft material, such as a rubber. As seen from a top view, as shown in FIG. 10C, protuberances 1040 are arranged in two concentric rings. The protuberances in the inner ring each include a wire electrode 1020 which protrudes from the tip of the respective protuberance. The protruding wire electrodes can be relatively short, reducing possible user discomfort due to the excessive pressure on the user's scalp.

Referring to FIGS. 11A-11E, a further example of a sensor electrode 1100 includes a base 1110, wire electrodes 1120, a press stud electrode 1130, and a protective cap 1140 (e.g., a plastic cap). The cap can reduce the likelihood that the user's hair becomes ensnared in the electrode, e.g., where the electrodes are attached to the base.

In some implementations, "wet" sensors are used. Wet sensors are those in which an electrically-conducting gel, e.g., commercially-available gels such as ECI Electro-Gel from Electro-Cap International, Inc. or Spectra 360 from Parker Laboratories, facilitates electrical contact between the electrode and the user's scalp. In general, gel can be dispensed onto the user's scalp manually, e.g., by the user or a technician, or using an automated dispense mechanism. Furthermore, in some embodiments, gel can include an adhesive to promote adhesion of the sensor to the user's scalp. Adhesive gels can facilitate use of EEG systems in non-laboratory settings.

In certain embodiments, a wet sensor can include an element that facilitates release of the electrode from the user's scalp. A sensor release element provides a stimulus (e.g., a thermal stimulus, chemical stimulus, radiation stimulus) to reduce adhesion of the sensor to the user's scalp, e.g., by changing the adhesion properties of the gel and/or the properties of the sensor itself. Such sensor release elements can facilitate use of more aggressive adhesives in the gel than, for example, adhesives that would simply involve mechanical removal from the scalp, like a Band-Aid.

For example, referring to FIG. 12, an EEG system 1200 features a wet sensor 1220 that is coupled to a user 1201's scalp with a conductive gel 1230. EEG system 1200 includes an EEG controller 1210 (including, e.g., a bioamplifier as described above) and sensor 1220 connected by a lead 1215. As illustrated, sensor 1220 includes a sensor electrode 1222, a gel dispense element 1224, and sensor release element 1226. Sensor 1220 also includes an electrical connector 1228 to which lead 1215 is connected. Electrical connections (e.g., wires) connect sensor electrode 1222, gel dispense element 1224, and sensor release element 1226 to connector 1228.

Sensor electrode 1222 is an electrically-conductive element that is positioned sufficiently close to the user's skin to detect electrical activity in the user's brain. Typically, sensor electrode 1222 is composed of an electrically-conductive material, such as a conducting metal (e.g., copper, aluminum), a metal alloy, or non-metal electrically-conducting material (e.g., a conducting polymer). The shape and size of sensor electrode can vary. In some embodiments, sensor electrode 1222 includes a pin that extends from the outer wall of the sensor towards the user. Alternatively, or additionally, sensor electrode 1222 can include a layer of a conducting material coating the surface of the sensor facing the user.

During use, gel dispense element 1224 dispenses electrically-conductive gel 1230 which contains an adhesive. The adhesive in gel 1230 bonds the surface of sensor 1220 to user 1201's skin, maintaining electrical conduction between sensor 1220 and user 1201. The gel dispense element 1224 can automatically gel 1230 in small amounts based on signals from EEG controller 1210, optimizing electrical contact of the sensor to user 1201 and providing a comfortable experience to the user. Gel can be dispensed continuously or periodically while the sensor is in use.

In general, gel dispense element 1224 can use a variety of different mechanisms to dispense gel to the user's scalp. For example, in some embodiments, gel dispense element 1224 relies on a contract-driven release mechanism to dispense gel. For example, pressure of contact with a user's head causes gel to dispense from the sensor to a user's head. Gel dispense element 1224 can be purely mechanical in its applications of conductive gel using force to retract and extend a probe into a housing storing conductive gel, thereby creating a dispense pathway from the chamber through the access port at the first chamber wall. In other embodiments, as illustrated in FIG. 12, gel dispense element 1224 includes a mechanism 1232, e.g., a pump or an actuator, that can be in electrical communication with EEG controller 1210 by lead 1215. An electrical pathway can be formed from EEG controller 1210 to lead 1215 and then to gel dispense element 1224. EEG controller 1210 sends control signals to mechanism 1232 causing gel dispense element 1224 to dispense gel to the skin, e.g., scalp, of user 1201. Exemplary gel dispense elements are described below.

In general, the adhesive used in the gel should be miscible in the gel and not react adversely with the user's skin, while providing a desirable level of adhesive between the sensor and the user's skin. In some embodiments, acrylate-based adhesives, such as methacrylates and epoxy diacrylates (also known as vinyl resins) may be employed. Cyanoacrylate adhesives can also be used. In some embodiments, siloxane adhesives can be used. The adhesives may be, for example, a blend of Polyvinyl Alcohol with salt (e.g., NaCL or KCl).

Sensor release element 1226 facilitates easy and comfortable release of the sensor from a user's head by changing the properties of the adhesive in the gel or the properties of the sensor, or both. In general, the release mechanism employed by sensor release element 1226 depends on the nature of the adhesive used in the gel. Control signals from EEG controller 1210 activate sensor release element 1226 to facilitate delamination of sensor 1220 from user 1201 as described in detail below. Examples of specific release mechanisms are described below.

Figure 13A:
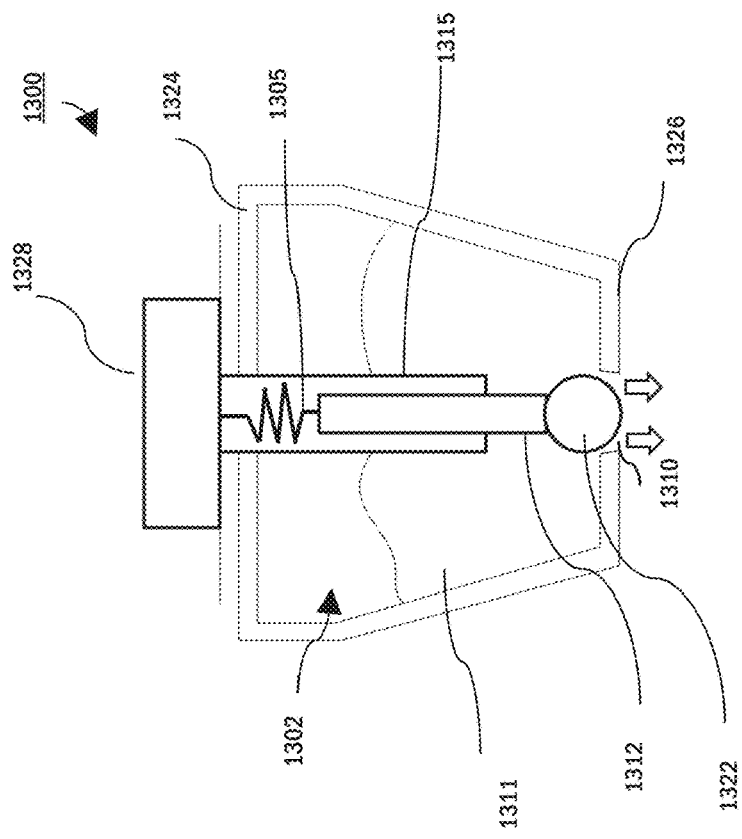
FIGS. 13A and 13B are cross-sectional schematic diagrams of an embodiment of an EEG sensor that automatically dispenses electrically conductive gel.
Figure 13B:
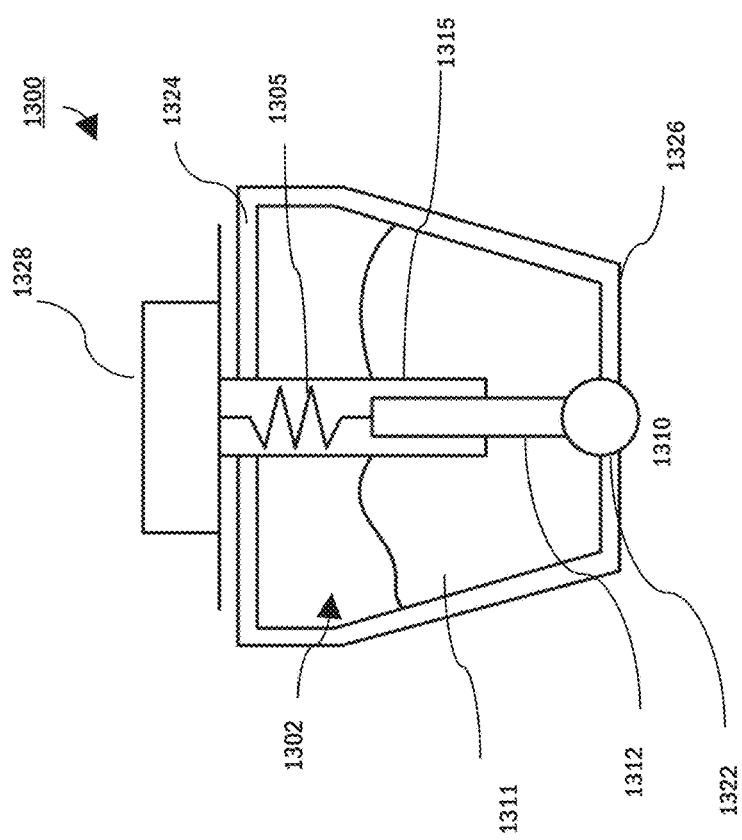

Referring to FIG. 13A and FIG. 13B, an example sensor 1300 with a gel dispense mechanism includes a single point probe 1312 extending through a reservoir 1302 containing conductive gel 1311. Sensor 1300 further includes a shaft 1315 that houses a spiral spring 1305 (or other compliant member) that connects probe 1312 to a lead connector 1328. Probe 1312, spring 1305, and connector 1328 provide an electrically-conductive pathway that extends from a wall 1326 of reservoir 1302 that faces the user through the reservoir's opposite wall 1324. Wall 1326 includes an aperture 1310 providing an access port to the gel reservoir. This aperture provides a dispense pathway. Probe 1312 includes a tip 1322 sized to seal aperture 1310. Accordingly, as shown in FIG. 13A, when spring 1305 is in an uncompressed state, probe 132 extends sufficiently far into reservoir 1302 so that tip 1322 seals aperture 1310, preventing flow of gel out of the reservoir. When pressure is applied to tip 1322, probe 1312 retracts into the reservoir, compressing spring 1305 and opening aperture 1310, thereby allowing flow of the gel out of the sensor as illustrated in FIG. 13B.

Figure 14:
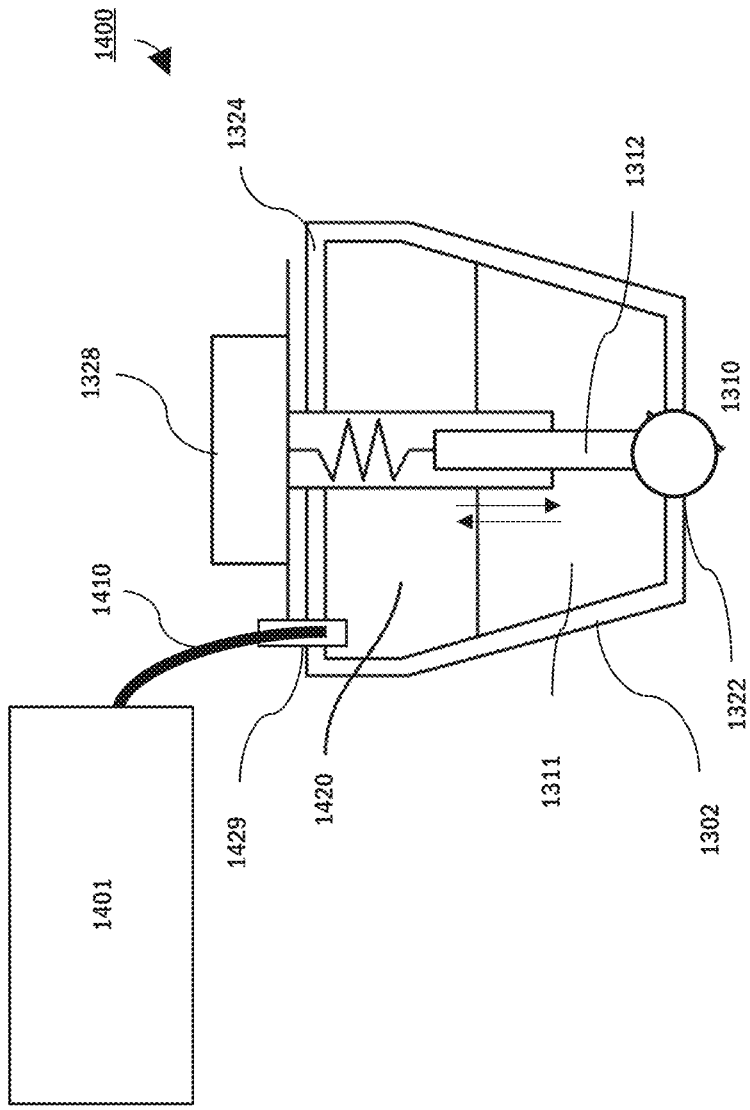
FIG. 14 is a cross-sectional schematic diagram of another embodiment of an EEG sensor that automatically dispenses electrically conductive gel.

Many types of gel have high viscosity and will not flow freely, particularly through a small aperture. Therefore, in some embodiments, a mechanism provides compression of the probe tip to actively constrain the gel cavity (e.g., put pressure on a bladder or a paddle) to compel the gel out of the opening. In other embodiments, the gel may be pressurized as described in FIG. 14.

Accordingly, when probe sensor 1300 is in contact with the user's skin, gel can be dispensed simply by applying pressure on the sensor sufficient to push the probe back into the reservoir. Once the pressure is removed, force from spring 1305 pushes probe tip 1322 back to seal aperture 1310, stopping gel flow to the user's skin.

In other embodiments, EEG sensor 1300 dispenses gel in response to signals from the EEG controller. For example, the EEG controller can monitor the quality of EEG signals measured using sensor 1300 and cause gel to dispense once the signal quality reduces past a pre-set threshold. Alternatively, or additionally, EEG sensor 1300 can monitor an electrical impedance at the user's scalp and cause gel to dispense when impedance exceeds a pre-set threshold. Above the pre-set threshold value, the EEG sensor can dispense either a standard volume of additional gel or continually dispense gel until the impedance is again below the threshold value.

In some embodiments, the EEG sensor needs an additional restriction to the dispense logic in order to identify whether the sensor is sufficiently close to a user's scalp. Dispensing gel will not improve signal quality or impedance if the sensor is not close to the user. The additional determination regarding proximity to a user's scalp may require an additional sensor, such as a temperature sensor to indicate proximity to skin, an accelerometer to indicate that motion of the sensor no longer matches to motion of other sensors, or an optical sensor to indicate that the sensor sees light and is therefore not flush against the scalp.

Additionally or alternatively, in some embodiments, software logic can determine if dispensing a small amount of gel changes the impedance or signal quality. If not, the logic can give up and send an error signal.

In embodiments which feature automatic dispensing, the sensor can include an electro-mechanical actuator (e.g., a piezo-electric actuator) in place of or in addition to spring 1305 which causes retraction and extension of the probe to open and seal aperture 1310.

The components of sensor 1300 are formed from materials and by methods suitable for their purposes. For example, probe 1312 is formed from a rigid, electrically-conductive material, such as a metal or metal-coated plastic. Chamber 1302 may be made out of plastic, e.g., printed using a 3D printer. Generally, the size and shape of the sensor are selected so that the reservoir is sufficiently large to hold gel commensurate with the length of time the system is in use, while being sufficiently small so that the sensor is reasonably unobtrusive and comfortable for extended use. For example, the reservoir can hold sufficient gel for an hour or more of continuous use (e.g., 8-10 hours). In some embodiments, the reservoir has a volume in a range from about 1 ml to about 10 ml.

In general, each gel dispense causes the sensor to dispense sufficient gel to provide adequate electrical-conductivity between the sensor and the user's skin. This can depend on, e.g., the nature of the gel, the size of the probe tip, among other factors. Generally, the probe dispenses sufficiently small volumes of gel so as not to wet a larger area of the user's scalp than is necessary. In certain embodiments, the sensor can dispense a fraction of a milliliter to a few milliliters in each event (e.g., 0.05 ml or more, 0.1 ml or more, 0.5 ml or more, 1 ml or more, such as 10 ml or less, 5 ml or less, 2 ml or less).

In some embodiments, a feedback system is used to continuously or periodically dispense gel during an extended period of sensor use to maintain good electrically connectivity of the sensor during the use period.

In some embodiments, the reservoir can be pressurized to facilitate dispensing the gel through the aperture. For example, referring to FIG. 14, an EEG sensor 1400 includes a volume of pressurized gas 1420 the portion of reservoir 1302 not filled by gel 1311. The gas pressure in the reservoir forces gel 1311 out of aperture 1310 when probe 1312 retracts tip 1322 into the reservoir.

Sensor 1400 includes a gas source (e.g., a pump and/or pressurized gas cylinder) 1401 that in connected to reservoir 1302 via a tube 1410. Manual pumps (e.g., a syringe) or electromechanical pumps can be used, for example. The tube connects to reservoir 1302 at a port 1429 in wall 1324. The connection to gas source 1401 ensures that the gas pressure in reservoir 1302 is maintained at sufficient pressure as the volume of gel in the chamber reduces.

Figure 15:
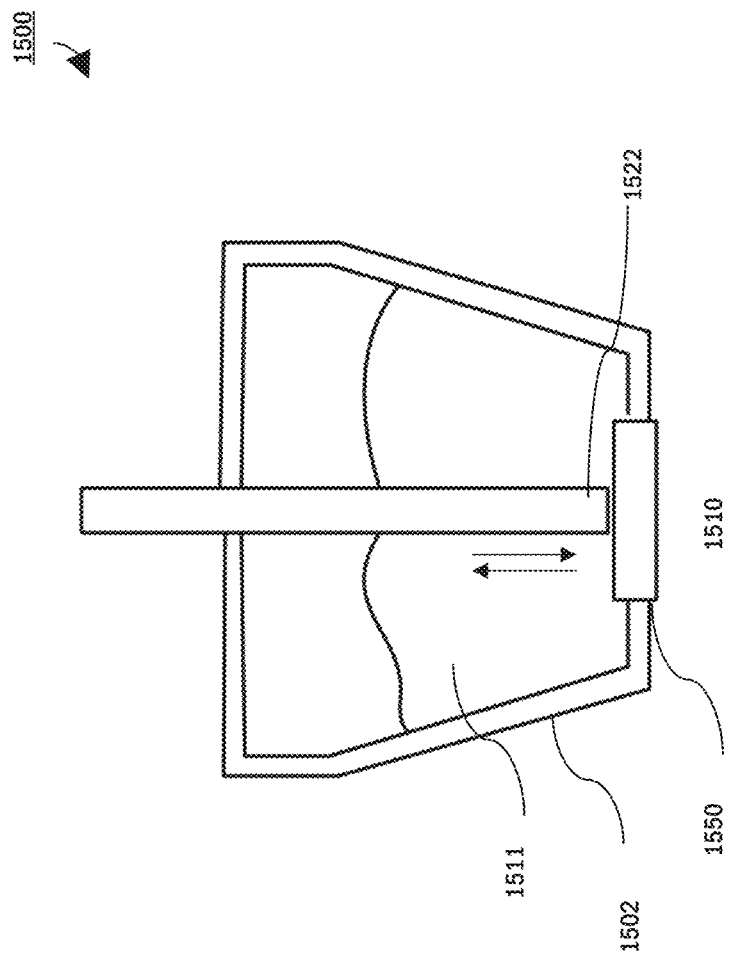
FIG. 15 is a cross-sectional schematic diagram of yet another embodiment of an EEG sensor that automatically dispenses electrically conductive gel.

Referring to FIG. 15, in an implementation of an EEG sensor 1500, rather than penetrate through an aperture, or access port, in a reservoir 1502, the base of chamber 1502 includes a sponge (or some other gel-permeable material) 1550 that facilitates transport of gel 1511 from chamber 1502 to user 1510's skin. The end of probe 1522 contacts the internal surface of sponge 1550 and may compress sponge 1550 against user 1510's skin. Sponge 1550 absorbs electrically conductive gel from chamber 1502 and coats user 1510's skin with the gel when the user 1510 presses against the sponge. Probe 1522 has a first wall that compresses against the sponge and a second wall that, although not shown, is electrically-connected to a lead. The lead is connected to an EEG controller, creating an electrical pathway from the probe to the EEG controller.

Figure 16:
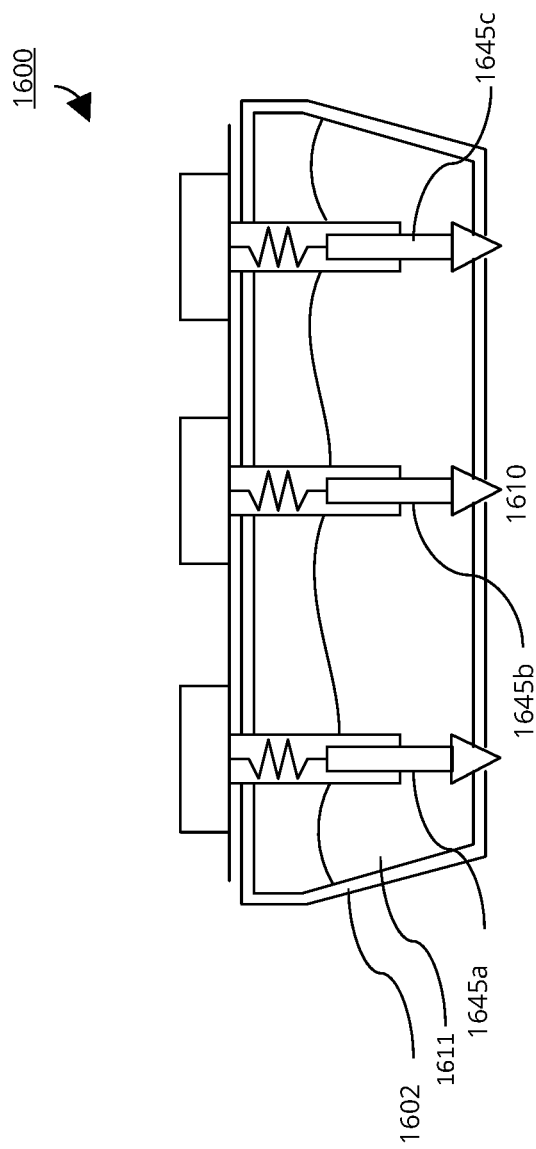
FIG. 16 is a cross-sectional schematic diagram of an embodiment of an EEG sensor that includes multiple probes connected to a single chamber that automatically dispense electrically conductive gel.

Referring to FIG. 16, in addition to having a single probe connected to a single reservoir housing chamber, an example implementation may have multiple probes 1645*a-c* connected to a single chamber 1602 as illustrated. Each probe separately engages a user 1610's skin. However, the probes 1645*a-c* share a common reservoir from which they draw conductive gel, and in some implementations pressurized gas or liquid. Chamber 1602 may contain gel 1611 only or may contain both gel 1611 and a pressurized element as described above with respect to FIG. 14. The multiple probes may be purely mechanical, e.g., spring-loaded, or they may be automatically controlled by an EEG controller. Alternatively, the probes may be connected to a gel-permeable material that facilitates transfer of the conductive gel to a user's skin as described above with respect to FIG. 15. In some implementations, multiple probes are placed in a headband or other headgear so that the probes are easy to affix to a user's head.

Generally, a chamber for an EEG sensor that holds conductive gel may be refillable at the tip of the probe, e.g., using a syringe. Alternatively, or additionally, conductive gel may be pumped through a separate inlet into the chamber. For example, referring to FIG. 14, although inlet 1429 is described as being used only for pressurized gas or liquid, this inlet may also be used to pump in conductive gel.

Turning now to examples of sensor release elements, in some embodiments, the gel includes an adhesive, which can be thermally released. For example, the gel can contain an adhesive which has adhesive properties that degrade at elevated temperatures and/or the gel can evaporate with application of heat. Accordingly, in some embodiments and with reference to FIG. 17A, a sensor 1720*a* includes a sensor release element that features a heating element 1771, e.g., a heating coil, which heats gel between sensor 1720 and the user's skin upon activation. Depending on the nature of the gel, heating element 1771 causes release of a gel 1230 in a variety of ways. For example, in FIG. 17A, heating element 1771 facilitates evaporation of a component of gel 1230 to cause release. Alternatively, or additionally, the heating can degrade or otherwise chemically alter the adhesive in gel 1230 so that adhesion of the sensor to the user's skin is reduced.

Heating element 1771 may be located close to an access point, or aperture, of sensor 1720*a* to emit heat from the sensor through the aperture to evaporate a portion or all of conductive gel 1230.

The EEG controller can send signals to heating element 1771 to control operation of heating element 1771 to time heat application with the desired release. Release can be prompted by the user, e.g., by entering a command via an input interface in communication with the EEG controller.

Heating element 1771 can alternatively maintain a gel component in an adhesive phase at an elevated temperature and, upon cessation of heating, cause release. Again, heating element 1771 may be located close to an access point, or aperture, of sensor 1720*a* to emit heat from the sensor through the access point to heat conductive gel 1230 and facilitate release. The EEG controller determines when and by how much to decrease or increase the temperature of the heating element 1771 in order to release the sensor from a user's head.

In general, thermal release should be performed at temperatures that are comfortable for the user. For example, the transition from adhesive to non-adhesive gel should occur at a temperature that is greater than body temperature but less than a temperature at which the user's skin will burn or otherwise experience pain. In some embodiments, this temperature can be in a range from 100° F. to about 120° F.

Figure 17B:
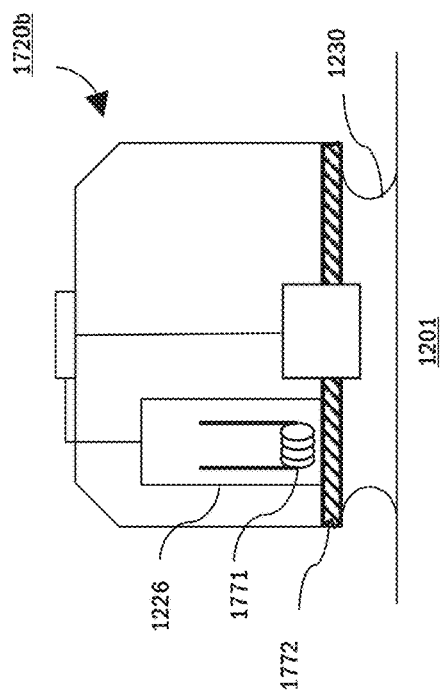
FIG. 17B is a cross-sectional schematic diagram of an embodiment of an EEG sensor that contains an automatic release mechanism.
Figure 17A:
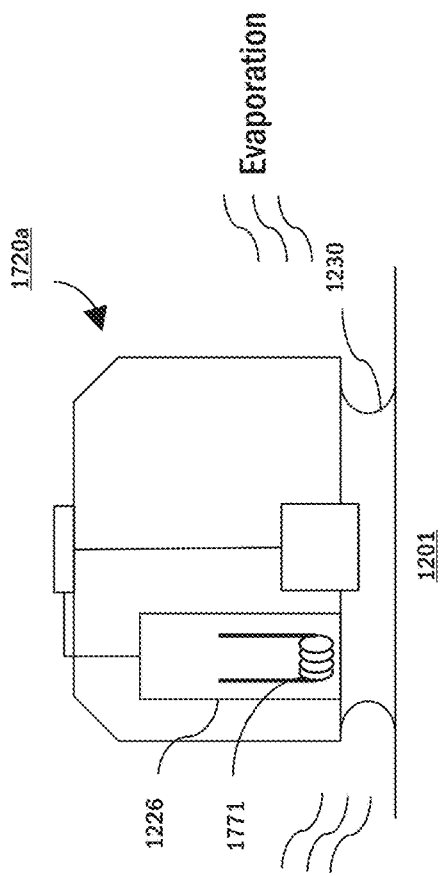
FIG. 17A is a cross-sectional schematic diagram of an embodiment of an EEG sensor that contains an automatic release mechanism.

In some embodiments, as illustrated in FIG. 17B, heating element 1771 operates in concert with a hygroscopic material 1772 to cause the material to absorb and/or release water to control the adhesive properties of gel 1230. Hygroscopic material 1772 may heat up from heating element 1771 and may absorb conductive gel 1230 through an access point of sensor 1720b. Additionally or alternatively, hygroscopic material 1772 can release a liquid, e.g., water, through the aperture of the sensor to detach the sensor from the user's head. EEG controller 1210 sends a signal through an electrical pathway from the controller to lead 1215 and to sensor release element 1226 containing heating element 1771. This signal initiates detachment of the sensor from the user by causing a change in temperature of the heating element. This change of temperature causes the hygroscopic material to heat or cool in a manner that delaminates the sensor from the user's skin.

Figure 17C:
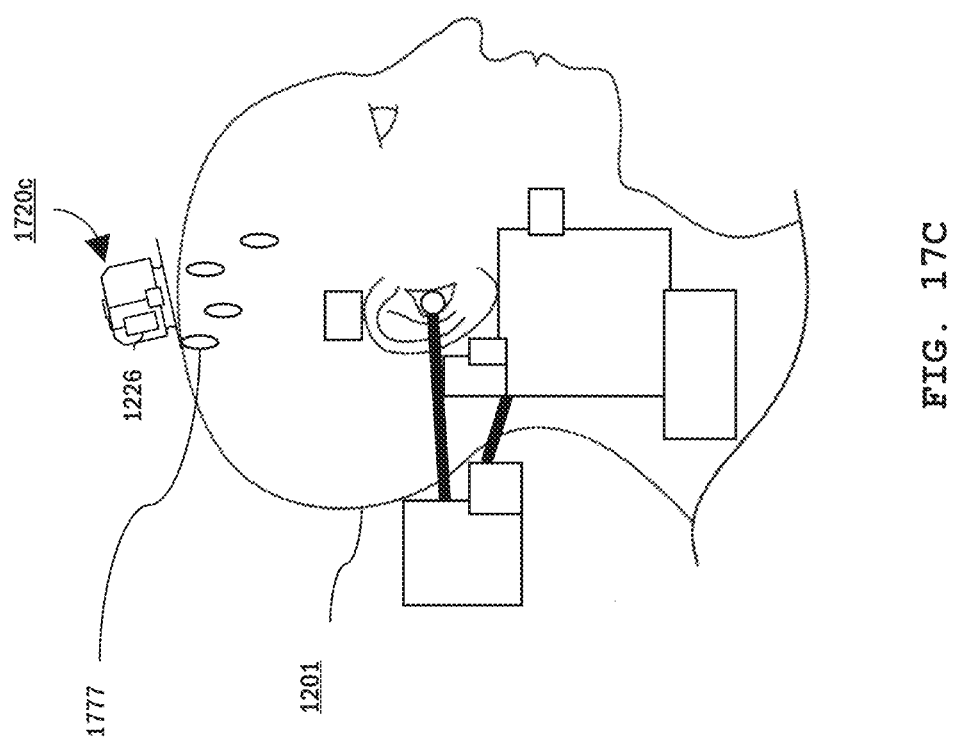
FIG. 17C is a cross-sectional schematic diagram of an embodiment of an EEG sensor that contains an automatic release mechanism.

FIG. 17C shows a sensor 1720c including a heating element 1771 on a user's 1201 head. Heating element 1771 causes user 1201 to sweat 1777, which then causes gel 1230 to release as illustrated.

Figure 17E:
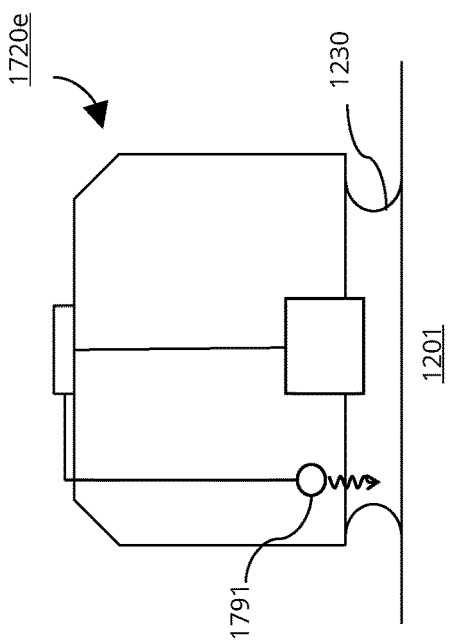
FIG. 17E is a cross-sectional schematic diagram of an embodiment of an EEG sensor that contains an automatic release mechanism.
Figure 17D:
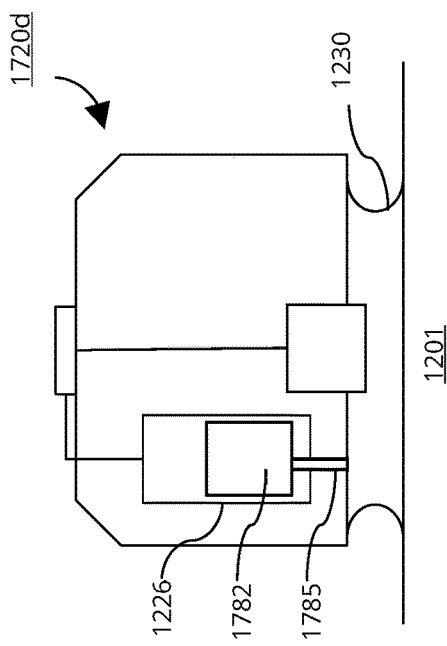
FIG. 17D is a cross-sectional schematic diagram of an embodiment of an EEG sensor that contains an automatic release mechanism.

In some implementations, a sensor release element contains a solvent dispenser 1782 as illustrated in FIG. 17D. A solvent dispenser 1782 may be a dispenser, e.g., a microfluidic pump, that dispenses a solvent into gel 1230 to facilitate release from user 1201's skin by dissolving (or otherwise physically and/or chemically reacting with) the adhesive in the gel. Solvent dispenser 1782 delivers the solvent through a channel 1785 that connects solvent dispenser 1782 with the outer surface of sensor 1720d.

In general, the solvent is selected based on the chemistry of the adhesive in the gel and its compatibility with a person's skin. In some embodiments, water is sufficient. In certain embodiments, the solvent is an organic solvent, such as alcohol. Surfactants can also be used to change the surface chemistry of the gel. For example, anionic, amphoteric, or cationic surfactants can be used to alter the interaction of the gel with the user's skin, facilitating release. Examples of surfactants include sodium lauryl sulfate, ammonium laureth sulfate, disodium lauryl sulfosuccinate, Cocoamphocarboxyglycinate, decyl Polyglucoside, cetearyl alcohol, stearyl alcohol, Cocamidopropyl Betaine, Decyl Glucoside, Glyceryl Cocoate, Sodium Cocoyl Isethionate, Almond Glycerides, Sodium Lauryl Sulphoacetate, Sodium Lauroyl Sarcosinate, sodium methyl cocoyl taurate, Sucrose Cocoate, and polysorbate.

Referring to FIG. 17E, sensor release element 1226 of FIG. 12 may contain a light source 1791, e.g., an ultraviolet (UV) LED with a wavelength selected to cause bond formation or bond breaking in the adhesive in gel 1230. For example, UV-curing adhesives or UV-degrading adhesives can be used. In some embodiments, an infrared light source can be used to heat the gel.

Figure 17F:
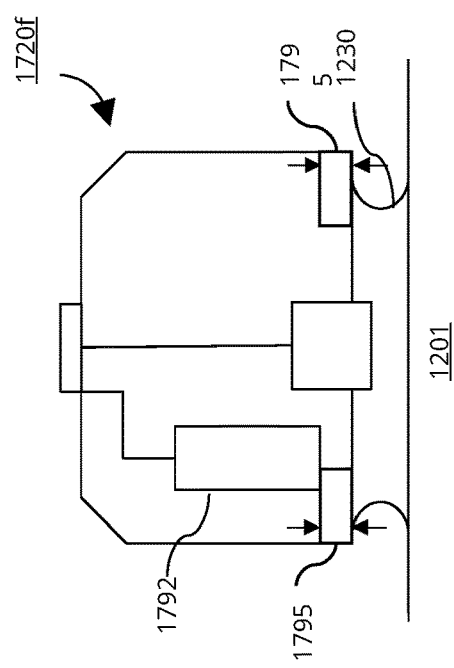
FIG. 17F is a cross-sectional schematic diagram of an embodiment of an EEG sensor that contains an automatic release mechanism.

Referring to FIG. 17F, in some embodiments, a sensor release element 1792 includes an actuator 1795 (e.g., a piezo electric actuator) that changes a shape of the contact surface to cause delamination of a sensor 1720f from user 1701's skin. For example, activation by a signal from the EEG controller can cause actuator 1795 to reduce its dimension in the direction shown by the arrows in FIG. 17F. This compression causes the edges of sensor 1720f to pull away from user's skin 1201, thereby facilitating delamination from the sensor.

In some embodiments, sensor 1220 may include only one of a gel dispense element 1224 or a sensor release element 1226. When gel dispense element 1224 is not included in sensor 1220, adhesive gel can be applied manually, e.g., by a technician or by the user directly. Furthermore, when sensor release element 1226 is not included in sensor 1220, sensor 1220 can be removed from user 1201's skin manually.

In general, the EEG systems described above can be used to accomplish a variety of computer-based tasks. For example, the disclosed system and techniques can be used to perform tasks commonly performed using a networked computer device (e.g., a mobile phone), such as ordering food, scheduling a flight, interacting with household or personal electronic devices, and/or purchasing a ticket for an event. The system can be used for user interaction with objects that have QR codes, bar codes, NFC tags, or another type of identification feature on them so that a system can detect the object with which the user is interacting and determine tasks associated with the object. These can be objects in a user's home such as a thermostat, television, phone, oven, or other electronic device. By way of example, an automated pet door in the user's house may have an associated QR code. By receiving the QR code from the dog door, the system may determine that the user is interacting with the door with their mobile phone. The system then can present the user with a list of options associated with the pet door on their phone. The system can then collect and analyze the user's EEG signals to determine what action the user would like the system to perform, in this example, whether or not to lock the pet door. Similarly, a system (e.g., EEG system 100) may use a user's phone or other computing device to notice proximity of a smart device. Proximity can be recognized by wireless or wired connectivity, (e.g., Bluetooth®, near field communication, RFID, or GPS). Once proximity is determined, the system can present the user with a choice related the smart device. For example, a user's phone may be able to notice that it is in proximity to a smart thermostat, such as a Nest®, a Honeywell® Lyric Round, or a Netatmo's thermostat, and then present the user with a choice about whether the user would like the temperature to be warmer or colder. Using the EEG decision making protocol described above, the system could then adjust the temperature in the room on the basis of the user's EEG, without the user having to physically interact with the thermostat. Any other two choice decision that can be made for a smart device (e.g., a smart home device such as an Amazon Alexa®, Google Home®, or WEMO® plug device) could be implemented in the same way—for example turning a smart light on or off, turning the volume of a smart speaker up or down, or making a decision to buy or not to buy what is in a digital shopping cart.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively, or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone, running a messaging application, and receiving responsive messages from the user in return.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

Figure 18:
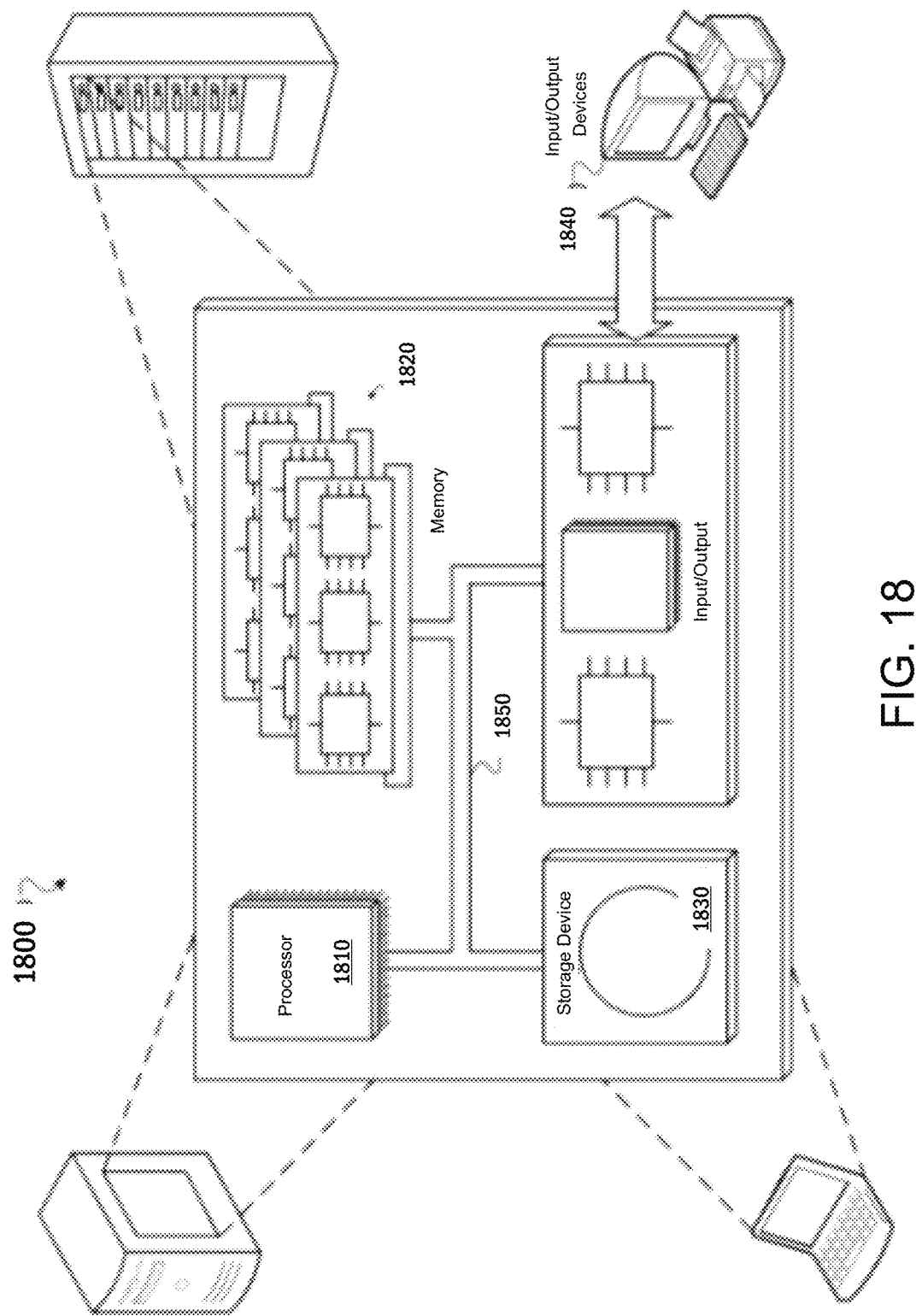
FIG. 18 is a schematic diagram of a data processing apparatus that can be incorporated into an EEG system.

An example of one such type of computer is shown in FIG. 18, which shows a schematic diagram of a generic computer system 1800. The system 1800 can be used for the operations described in association with any of the computer-implemented methods described previously, according to one implementation. The system 1800 includes a processor 1810, a memory 1820, a storage device 1830, and an input/output device 1840. Each of the components 1810, 1820, 1830, and 1840 are interconnected using a system bus 1850. The processor 1810 is capable of processing instructions for execution within the system 1800. In one implementation, the processor 1810 is a single-threaded processor.

In another implementation, the processor 1810 is a multi-threaded processor. The processor 1810 is capable of processing instructions stored in the memory 1820 or on the storage device 1830 to display graphical information for a user interface on the input/output device 1840.

The memory 1820 stores information within the system 1800. In one implementation, the memory 1820 is a computer-readable medium. In one implementation, the memory 1820 is a volatile memory unit. In another implementation, the memory 1820 is a non-volatile memory unit.

The storage device 1830 is capable of providing mass storage for the system 1800. In one implementation, the storage device 1830 is a computer-readable medium. In various different implementations, the storage device 1830 may be a floppy disk device, a hard disk device, an optical disk device, or a tape device.

The input/output device 1840 provides input/output operations for the system 1200. In one implementation, the input/output device 1840 includes a keyboard and/or pointing device. In another implementation, the input/output device 1840 includes a display unit for displaying graphical user interfaces.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

As used herein, the term "real-time" refers to transmitting or processing data without intentional delay given the processing limitations of a system, the time required to accurately obtain data and images, and the rate of change of the data and images. In some examples, "real-time" is used to describe concurrently receiving, cleaning, and interpreting EEG signals. Although there may be some actual delays, such delays generally do not prohibit the signals from being cleaned and analyzed within sufficient time such that the data analysis remains relevant to provide decision-making feedback and accomplish computer-based tasks. For example, adjustments to a smart thermostat are calculated based on user EEG signals. Cleaned signals are analyzed to determine the user's desired temperature before enough time has passed to render the EEG signals irrelevant.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous. Wireless or wired connections may be advantageous for different use cases. Miniaturized components may replace existing components. Other data transmission protocols than those listed may be developed and implemented. The nature of the ML systems used for both data cleaning and classification may change.

What is claimed is:

1. An electroencephalogram (EEG) sensor, comprising:
   a housing defining a chamber storing a gel, the housing comprising an aperture in fluidic communication with the chamber allowing gel to be dispensed therethrough;
   a hollow shaft housing a spring and an electrically-conductive probe, wherein the spring is arranged to exert a force on the electrically-conductive probe such that the spring biases a tip of the probe to seal the aperture through which gel is dispensed from the chamber, and wherein retraction of the probe tip into the chamber unseals the aperture forming a gel dispense pathway, thereby permitting gel to flow from the chamber out of the aperture; and
   an electrical terminal located at an outer surface of the chamber, the electrical terminal being in electrical communication with the probe tip.

2. The EEG sensor of claim 1, wherein the spring is mechanically attached to the electrically-conductive probe.

3. The EEG sensor of claim 1, wherein the spring and electrically-conductive probe are arranged so that axial pressure applied to the tip causes the tip to retract into the chamber and compress the spring.

4. The EEG sensor of claim 1, wherein the electrical terminal is a connector for connecting to an electrical lead.

5. The EEG sensor of claim 1, wherein the chamber comprises one or more additional apertures each defining a corresponding dispense pathway.

6. The EEG sensor of claim 1, further comprising an actuator operably coupled to the probe and in electrical communication with an EEG controller, the actuator configured to retract the probe to open the gel dispense pathway in response to control signals from the EEG controller.

7. The EEG sensor of claim 6, wherein the EEG controller is configured to:
   monitor a quality of EEG signals received from the EEG sensor; and
   responsive to the quality of the EEG signals, selectively control the actuator to dispense additional electrically-conductive gel.

8. The EEG sensor of claim 1, wherein the chamber has a volume between 1 ml to 10 ml.

9. The EEG sensor of claim 1, wherein the hollow shaft is disposed within the chamber.

10. An apparatus, comprising:
    the EEG sensor of claim 1; and
    a pump in fluid communication with the chamber, the pump being arranged to apply pressure to the gel stored in the chamber.

11. The apparatus of claim 10, wherein the pump is configured to supply gel to the chamber.

12. The apparatus of claim 10, wherein the pump is configured to supply pressurized gas to the chamber.

13. The apparatus of claim 10, wherein the pump is a manual pump.

14. The apparatus of claim 10, wherein the pump is an electro-mechanical pump.

15. The apparatus of claim 10, wherein the pump is in fluid communication with the chamber via a fluid channel.

16. An electroencephalogram (EEG) sensor, comprising:
   a housing defining a chamber storing a gel;
   at least two probe assemblies disposed within the chamber, wherein each probe assembly comprises: a hollow shaft housing a spring and an electrically-conductive probe, wherein the spring is arranged to exert a force on the electrically-conductive probe such that the spring biases a tip of the probe to seal a corresponding aperture formed in the housing and through which gel is dispensed from the chamber, and wherein retraction of the probe tip into the chamber unseals the respective one of the apertures forming a gel dispense pathway, thereby permitting gel to flow from the chamber out of the corresponding aperture; and
   two or more electrical terminals corresponding with the at least two probe assemblies, wherein each electrical terminal is in electrical communication with the probe tip of a corresponding one of the probe assemblies.

17. The EEG sensor of claim 16, further comprising an actuator operably coupled to each of the probes of the probe assemblies and in electrical communication with an EEG controller, the actuator configured to retract the probes to open the gel dispense pathways in response to control signals from the EEG controller,
   wherein the EEG controller is configured to:
      monitor a quality of EEG signals received from the EEG sensor; and
      responsive to the quality of the EEG signals, selectively control the actuator to dispense additional electrically-conductive gel.

18. An electroencephalogram (EEG) sensor system, comprising:
   an EEG controller; and
   at least one EEG sensor communicably coupled to the EEG controller, wherein each EEG sensor comprises:
      a housing defining a chamber storing a gel, the housing comprising an aperture in fluidic communication with the chamber allowing gel to be dispensed therethrough;
      a hollow shaft housing a spring and an electrically-conductive probe, wherein the spring is arranged to exert a force on the electrically-conductive probe such that the spring biases a tip of the probe to seal the aperture through which gel is dispensed from the chamber, and wherein retraction of the probe tip into the chamber unseals the aperture forming a gel dispense pathway, thereby permitting gel to flow from the chamber out of the aperture;
      an electrical terminal in electrical communication with the probe tip; and
      an actuator operably coupled to the probe, the actuator configured to retract the probe to open the gel dispense pathway in response to control signals from the EEG controller.

19. The EEG sensor of claim 18, wherein the EEG controller is configured to:
   monitor a quality of EEG signals received from the at least one EEG sensor; and
   responsive to the quality of the EEG signals, selectively control a corresponding actuator of the at least one EEG sensor to dispense additional electrically-conductive gel.

* * * * *